United States Patent
Parthasarathy et al.

(10) Patent No.: US 9,320,834 B2
(45) Date of Patent: Apr. 26, 2016

(54) HARDENABLE ANTIMICROBIAL COMPOSITION

(71) Applicant: 3M INNOVATIVE PROPERTIES COMPANY, St. Paul, MN (US)

(72) Inventors: Ranjani V. Parthasarathy, Woodbury, MN (US); John M. Heapy, St. Paul, MN (US); Vinod P. Menon, Woodbury, MN (US); Matthew T. Scholz, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 14/412,808

(22) PCT Filed: Jul. 2, 2013

(86) PCT No.: PCT/US2013/049072
§ 371 (c)(1),
(2) Date: Jan. 5, 2015

(87) PCT Pub. No.: WO2014/008264
PCT Pub. Date: Jan. 9, 2014

(65) Prior Publication Data
US 2015/0165097 A1    Jun. 18, 2015

Related U.S. Application Data

(60) Provisional application No. 61/668,356, filed on Jul. 5, 2012, provisional application No. 61/766,328, filed on Feb. 19, 2013.

(51) Int. Cl.
*A61L 31/04* (2006.01)
*A01N 25/10* (2006.01)
*C08K 5/19* (2006.01)
*A61L 31/14* (2006.01)
*A61L 31/16* (2006.01)
*C08K 5/00* (2006.01)

(52) U.S. Cl.
CPC ............... *A61L 31/048* (2013.01); *A01N 25/10* (2013.01); *A61L 31/141* (2013.01); *A61L 31/143* (2013.01); *A61L 31/16* (2013.01); *C08K 5/0058* (2013.01); *C08K 5/19* (2013.01); *A61L 2300/404* (2013.01); *A61L 2300/602* (2013.01); *A61L 2300/802* (2013.01); *C08K 5/0016* (2013.01); *C08K 5/0066* (2013.01)

(58) Field of Classification Search
CPC .............................. A61L 31/04; A61L 31/048
USPC .......................................................... 514/340
See application file for complete search history.

(56) References Cited

U.S. PATENT DOCUMENTS

| | | |
|---|---|---|
| 5,069,907 A | 12/1991 | Mixon |
| 5,084,096 A | 1/1992 | Stovicek |
| 5,091,442 A | 2/1992 | Milner |
| 5,111,904 A | 5/1992 | Packard |
| 5,324,471 A | 6/1994 | Packard |
| 5,380,182 A | 1/1995 | Packard |
| 5,408,022 A | 4/1995 | Imazato |
| 5,725,867 A * | 3/1998 | Mixon .................. 424/402 |
| 6,440,405 B1 | 8/2002 | Cooper |
| 7,179,849 B2 | 2/2007 | Terry |
| 8,198,326 B2 | 6/2012 | Scholz |
| 8,512,723 B2 | 8/2013 | Scholz |
| 2005/0058673 A1 | 3/2005 | Scholz |
| 2006/0051384 A1 | 3/2006 | Scholz |
| 2008/0275113 A1 | 11/2008 | Huetter |
| 2008/0279907 A1 | 11/2008 | Ash |
| 2011/0190665 A1 | 8/2011 | Bedingham |

FOREIGN PATENT DOCUMENTS

| | | |
|---|---|---|
| KR | 10-2007-0071028 | 7/2007 |
| WO | WO 96-29361 | 9/1996 |
| WO | WO 02-102244 | 12/2002 |

OTHER PUBLICATIONS

Block, "Disinfection, Sterilization and Preservation", 4th Edition, pp. 225-255 (1991).
International Search Report for PCT International Application No. PCT/US2013/049072 mailed on Sep. 25, 2013, 4 pages.

* cited by examiner

*Primary Examiner* — Taofiq A Solola

(57) ABSTRACT

The present disclosure provides antimicrobial compositions including a polyhaloolefin polymer, a cationic antimicrobial agent, and a vehicle that includes a plasticizer and a heat stabilizer. The cationic antimicrobial agent can be partially soluble in the vehicle. The present disclosure also provides for articles formed from the composition, with cationic antimicrobial agent incorporated throughout the polymer matrix, as well as methods of manufacturing the composition.

10 Claims, No Drawings

HARDENABLE ANTIMICROBIAL COMPOSITION

BACKGROUND

The presence of pathogenic organisms in biological fluids and tissue is of continuous concern, as is the potential for transfer of such organisms to and from the surfaces of medical articles. This transfer can be particularly problematic in hospitals or other care facilities, as certain medical articles may be exposed to multiple individuals or remain in situ for long periods without adequate cleaning. Even if certain medical personnel hygiene protocols are rigorously followed, the exposed surfaces of these devices may still attract pathogenic organisms by virtue of a continuous or semi-continuous proximity to pathogen bearing individuals or substrates. For at least these reasons, methods for minimizing the transmission of pathogens from medical article surfaces to human tissue are of significant importance.

Attempts have been made to provide medical article surfaces that are inherently antimicrobial, either by composition or use of antimicrobial drug delivery systems. These surfaces can be insufficiently effective in reducing transfer for at least four potential reasons: 1) when used as a delivery system, antimicrobial or active agents may be exhausted well before the end of the service lifetime of the medical article; 2) the surface antimicrobial properties are eventually impaired as dead cells, high organic load, and other adsorbed debris mask the antimicrobial properties of that surface; 3) antimicrobial agents in the material or in an external coating fail to elute sufficiently; 4) the antimicrobial agent is unsafe for human tissue contact; and 5) antimicrobial kill may take too long to develop.

Polyhaloolefins, including polyvinyl chloride polymers, have proven particularly useful in constructing many medical articles, including stethoscopes. Attempts have been made to imbue polyhaloolefin plastisols with antimicrobial or biocidal agents. The antimicrobial agent, such as triclosan, is typically mixed with the polymeric resin prior to forming said medical article in an attempt to impart controlled release of the antimicrobial agent.

SUMMARY

Recent studies suggest that triclosan may cause endocrine disruption in the body, rendering its use as a continuously active antimicrobial problematic for many skin-contacting applications. Incorporation of less disruptive antimicrobial agents, such as cationic antimicrobial agents can result in degradation of the polyhaloolefin polymer. Further issues associated with cationic antimicrobials include their own degradation at high processing temperatures and an attendant reduced antimicrobial efficacy. Furthermore, certain cationic materials are typically expected to be highly incompatible with an organic polymer matrix. For example, the present inventors discovered that if cationic antimicrobials such as benzalkonium chloride and cetylpyridinium chloride are added to commercially available PVC plastisols the resulting cured PVC article is severely degraded, with an apparent color that is very dark or in some circumstances black. Thus, what is needed is a polymer composition that can impart prolonged antimicrobial activity upon hardening over substantially the entire treated surface and that may be cured without causing significant degradation of the polyhaloolefin polymer and/or the antimicrobial agent incorporated therein. In certain implementations of the present disclosure, it can be advantageous that other physical characteristics of the desired cured article (e.g., surface finish) are not substantially affected or changed by the addition of the antimicrobial.

The present disclosure provides antimicrobial compositions that include a polyhaloolefin polymer, a cationic antimicrobial agent, and a nonvolatile vehicle. The vehicle comprises at least a plasticizer and at least one heat stabilizer. The antimicrobial compositions of the present disclosure are hardenable, in that once a desired article (e.g., stethoscope tubing) or coating is formed from the compositions, they are allowed to harden (e.g., cure) to form stable, solid antimicrobial compositions. Surprisingly, the cationic antimicrobial agent is at least partially soluble in the vehicle compositions disclosed herein and therefore the composition maintains a prolonged, active kill upon hardening. In certain implementations, the hardened compositions are substantially free of volatile components (i.e., components that would evaporate at ambient conditions). Typically, these vehicles have boiling points in excess of 300° F. and even in excess of 390° F. at ambient pressure.

A hardened antimicrobial composition of the present disclosure can be in the form of a coating, self-supporting film, or a shaped article, for example. It can form a part of, for example a surgical face mask, respirator, or other breathing apparatus that contacts all or part of a facial contact area, a surgical drape, a dental appliance or other dental equipment; cosmetic applicator, sponge, contact lens, contact lens case, catheter (e.g., IV, umbilical artery, urinary catheter), endotracheal tube, intravenous (IV) bags and tubing, blood bags and infusion tubing, blood and fluid warming circuits, enteral nutrition feeding bags, nasogastric tubes, peritoneal dialysis bags and tubing, tubing used in various medical procedures (e.g., cardiopulmonary bypass (CPB) procedures, extracorporeal membrane oxygenation (ECMO) and hemodialysis), and a surgical glove. In a particularly suitable example, the hardened polymer composition form as least a portion of a stethoscope or an endotracheal tube.

In certain embodiments, the antimicrobial composition achieves at least 1 log reduction of a target microorganism in 2 hours when evaluated by the Antimicrobial Efficacy Test described below. In more desirable embodiments, the compositions achieve a 2 log reduction. In even more desirable embodiments, the compositions achieve a 3 log reduction. In certain embodiments, the target organisms comprise *Pseudomonas aeruginosa, Staphylococcus aureus, E. coli,* and methicillin-resistant *Staphylococcus aureus*. In certain embodiments, residual antimicrobial efficacy is provided to any surface formed from the hardened composition. In certain embodiments, the hardened composition provides an active kill for an extended period of time during the life of the article.

In some embodiments, the rate and duration of kill can be adjusted by controlling the solubility of the antimicrobial in the composition. For instance, if the solubility of the antimicrobial in the composition is below a certain threshold, more antimicrobial may be initially available at the surface, with less available from the polymer matrix over time. This may be a desirable feature for articles with a short useful life. In other cases, where toxicity is an issue, for example, an antimicrobial agent at lower concentrations but with higher solubility can be used.

In some advantageous implementations, compositions of the present disclosure do not substantially degrade during hardening, in that they show little to no indicia of antimicrobial agent or polymer degradation (e.g., substantial precipitate and/or substantial yellowing or blackening) after curing at 175° C. for 10 minutes. While certain embodied compositions may become slightly cloudy or yellow during the processing period, the absence of substantial color change and/or precipitation means these samples may be considered to have avoided substantial degradation of the matrix or the antimicrobial agent. Other compositions of the present disclosure show no visible changes, i.e., no changes in color or clarity upon curing.

In one aspect, the present disclosure provides a hardenable polyhaloolefin composition, the composition including: a polyvinyl chloride polymer; a cationic antimicrobial agent; a vehicle comprising a plasticizer; and a heat stabilizer, wherein the cationic antimicrobial is at least partially soluble in the vehicle.

In another aspect, the present disclosure provides an article comprising: an exposed surface at least partially formed from a hardened antimicrobial composition, the composition including a polyhaloolefin polymer, and a heat stabilizer, a plasticizer, and a cationic antimicrobial agent incorporated throughout the polymer.

In yet another aspect, the present disclosure provides a method of creating an antimicrobial composition, the method comprising: providing a vehicle including a plasticizer and a heat stabilizer; providing a cationic antimicrobial agent; providing a polyhaloolefin polymer dispersion; admixing the vehicle, the cationic antimicrobial, and the polymer to create a hardenable composition, the cationic antimicrobial is soluble in the vehicle to a concentration of at least 0.1 wt-%.

As used herein, "active kill" means to render a microorganism ineffective by killing (e.g., bacteria and fungi) or otherwise rendering inactive (e.g., viruses) and may be distinguished from disrupting microorganism adhesion or mere bacteriostatic activity. Typically, an active kill results in at least a 0.5 log reduction using the Antimicrobial Efficacy Test described herein, and is desirably at least a 1 log reduction, more preferably at least a 2 log reduction, even more preferably at least a 3 log reduction. It should be understood that in the compositions described herein, the concentrations or amounts of the components, when considered separately, may not kill to an acceptable level, or may not kill as broad a spectrum of undesired microorganisms, or may not kill as fast; however, when used together such components provide an enhanced (preferably synergistic) antimicrobial activity (as compared to the same components used alone under the same conditions).

As used herein, "customary use" refers to the typical use of an article that includes the hardened polymer compositions of the present disclosure. For example, the customary use of a stethoscope that includes tubing coated with, or made out of, an antimicrobial composition of the present disclosure includes placing the tubing against skin or clothing for prolonged periods and wiping the stethoscope periodically with an alcohol-saturated cloth/wipe or an aqueous wipe at room temperature.

The term "microorganism" is generally used to refer to any prokaryotic or eukaryotic microscopic organism, including without limitation, one or more bacteria (e.g., motile or vegetative, Gram positive or Gram negative), bacterial spores or endospores, algae, fungi (e.g., yeast, filamentous fungi, fungal spores), mycoplasmas, viruses, and protozoa, as well as combinations thereof. In some cases, the microorganisms of particular interest are those that are pathogenic, and the term "pathogen" is used to refer to any pathogenic microorganism. Examples of pathogens can include, but are not limited to, both Gram positive and Gram negative bacteria, fungi, and viruses including members of the family Enterobacteriaceae, or members of the family Micrococaceae, or the genera *Staphylococcus* spp., *Streptococcus*, spp., *Pseudomonas* spp., *Enterococcus* spp., *Salmonella* spp., *Legionella* spp., *Shigella* spp., *Yersinia* spp., *Enterobacter* spp., *Escherichia* spp., *Bacillus* spp., *Listeria* spp., *Campylobacter* spp., *Acinetobacter* spp., *Vibrio* spp., *Clostridium* spp., *Klebsiella* spp., *Proteus* spp. and *Corynebacterium* spp. Particular examples of pathogens can include, but are not limited to, *Escherichia coli* including enterohemorrhagic *E. coli* e.g., serotype O157: H7, O129:H11; *Pseudomonas aeruginosa; Bacillus cereus; Bacillus anthracia; Salmonella enteritidis; Salmonella enterica* serotype *Typhimurium; Listeria monocytogenes; Clostridium botulinum; Clostridium perfringens; Staphylococcus aureus*; methicillin-resistant *Staphylococcus aureus; Campylobacter jejuni; Yersinia enterocolitica; Vibrio vulnificus; Clostridium difficile*; vancomycin-resistant *Enterococcus; Klebsiella pnuemoniae; Proteus mirabilus* and *Enterobacter [Cronobacter] sakazakii*.

As used herein "partially soluble" means that the concentration of cationic antimicrobial dissolved or dispersed in the vehicle is at least 0.1 wt. %, based on the total weight of the vehicle.

As used herein, a "hardened polyhaloolefin composition" is a composition that has been cured (by e.g., heating) to form a stable, solid article and that includes at least one polyhaloolefin polymer, at least one plasticizer, at least one heat stabilizer, and at least one cationic antimicrobial agent. A "hardened polymer" can be achieved by solidifying a liquid polymer or polymer dispersion by heating. Other methods include crosslinking or otherwise curing a hardenable polymer to render it insoluble, by extruding or molding a polymer, etc. It does not necessarily mean that the polymer is hard and inflexible; rather it means that the polymer containing composition is cured or otherwise rendered solid. In fact, in certain applications such as coatings on flexible or deformable substrates a flexible "hardened" polymer composition may be preferred.

It should be understood that (unless otherwise specified) the listed concentrations of all components are for "ready to use" or "as used" compositions. The compositions can be in a concentrated form. That is, certain embodiments of the compositions can be in the form of concentrates that would be diluted by the user with an appropriate vehicle; however, this is typically not convenient for the present application.

The terms "comprises" and variations thereof do not have a limiting meaning where these terms appear in the description and claims.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As recited herein, all numbers should be considered modified by the term "about".

As used herein, "a," "an," "the," "at least one," and "one or more" are used interchangeably. Thus, for example, a plastisol comprising "a" heat stabilizer can be interpreted to comprise "one or more" heat stabilizers.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exhaustive list. In all cases, this disclosure presents the invention by way of representation and not limitation. It should be understood that numerous other modifications and embodiments can be devised by those skilled in the art, which fall within the scope and spirit of the principles of the invention.

DETAILED DESCRIPTION OF ILLUSTRATIVE EMBODIMENTS

The present disclosure provides a hardenable, antimicrobial polymer composition for use in forming myriad medical and industrial articles. The composition includes at least one active antimicrobial agent made to withstand degradation during the hardening of the polymer (i.e., curing). In certain advantageous implementations, the antimicrobial can maintain an active kill of certain target microorganism during and after customary use of the article. The compositions include a polyhaloolefin polymer, a cationic antimicrobial agent, and a vehicle. The vehicle includes a heat stabilizer package and a plasticizer. The vehicle typically does not include any volatile components and is defined as that portion of the composition other than the polyhaloolefin and antimicrobial agent. The heat stabilizer package can include one or more primary heat stabilizers, typically metal alkylcarboxylate salts such as zinc dioctoate, and one or more secondary heat stabilizers. In implementations particularly suitable for use in medical articles, the cationic antimicrobial is at least partially soluble in the vehicle. The vehicle, and thus the compositions, may further include secondary antimicrobial agents, as well as other additives.

A surface that includes a hardened antimicrobial composition of the present disclosure may have prolonged or durable antimicrobial activity, in that its ability to kill, inactivate, or otherwise limit the presence of target microorganisms is not substantially diminished by customary use of the surface (particularly surface cleaning). The present inventors have found, surprisingly, that certain combinations of heat stabilizer and plasticizers provide for enhanced solubility of normally insoluble or insufficiently soluble cationic antimicrobial agents in polyhaloolefin compositions. The enhanced solubility of the cationic antimicrobial agent can result in greater antimicrobial efficacy at the surface of an article at least partially formed from the hardened antimicrobial composition. By greater antimicrobial efficacy it is meant that there is greater initial bacterial log reduction and/or the article has more durable antimicrobial activity, i.e., retains more antimicrobial activity after customary use. Without wishing to be bound by theory, the enhanced solubility increases the likelihood that the antimicrobial agent will be available at an article surface at least partially formed from the hardened composition. Furthermore, the enhanced solubility may ensure that antimicrobial agents remain available in the polymer matrix, in addition to those on the surface that may be removed by e.g., a vigorous alcohol or aqueous wipe. The remaining availability of antimicrobial agents in the matrix can allow for prolonged antimicrobial activity through replenishment of the antimicrobial agent at the surface, though antimicrobial agents may not, in certain circumstances, be immediately available at the surface after that surface is wiped with alcohol or other aqueous solution. Typically, the antimicrobial agents will return to the surface in bactericidal amounts after 8 hours, preferably after 4 hours, more preferably after 2 hours, even more preferably after 30 minutes, and most preferably after 15 minutes.

Due at least partially to the availability of the cationic antimicrobial agent at the surface of the hardened compositions, the antimicrobial compositions of the present disclosure can achieve at least 1 log reduction in target microorganism in 2 hours when evaluated by the Antimicrobial Efficacy Test described in the Examples below. In more desirable embodiments, the compositions can achieve a 2 log reduction. In even more desirable embodiments, the compositions can achieve a 3 log reduction. In certain embodiments, the target organisms comprise *Pseudomonas aeruginosa, Staphylococcus aureus*; and methicillin-resistant *Staphylococcus aureus*.

Furthermore, the present inventors have found that antimicrobials that are normally unstable at high curing temperatures typically associated with forming certain medical articles, particularly stethoscope tubing, avoid aesthetic degradation when coupled with certain vehicles. Preferred compositions of the present disclosure do not substantially degrade during thermal processing (i.e., curing), in that they show little to no indicia of antimicrobial agent or polymer degradation (e.g., substantial yellowing or blackening and/or precipitate) after curing at about 350° F. for 10 minutes. While certain embodied compositions may become slightly cloudy or yellow during the processing period, the absence of gross separation and/or precipitation means these samples may be considered to have avoided substantial degradation. In certain embodiments, a lack of heat stabilizer may result in severe discoloration, turning the hardened composition dark brown or even black. Other compositions of the present disclosure show no visible changes, i.e., no changes in color or clarity upon curing.

As discussed above, the hardenable compositions of the present disclosure typically include: a polymer; a cationic antimicrobial agent; a heat stabilizer package comprising one or more heat stabilizing compounds; and a plasticizer. Each component of the antimicrobial composition is discussed in more detail below.

Polymer

In the case of the present disclosure, the polymer can comprise homopolymers of polyhaloolefins, (such as polyvinyl chloride) or copolymers of polyhaloolefins (such as polyvinyl chloride and vinyl acetate) or polymer blends. Suitable polymers include polyvinylchloride (PVC) dispersion plastisols available as GEON series of PVC homopolymer resins from PolyOne Corporation, Avon Lake, Ohio. A particularly suitable polymer is a polyvinylchloride (PVC) dispersion plastisol available as Geon 179. Dispersion resins are typically fine particles (avg. 0.1-1.5 μm) and could be used for homopolymers as well as copolymers of vinyl chloride and other monomers such as acetates and acrylates. Blending resins, average particle size from 25-75 μm, can also be used in conjunction with dispersion resins to control rheology and surface aesthetics. In some implementations, suspension resins can be used. The type of resin selected is generally based on properties such as particle size, distribution, molecular weight, copolymers etc. to allow for easy processing and to impart the desired aesthetics and mechanical properties. For example, Geon 179 is a high molecular weight homopolymer that can be made by a dispersion process. The properties of this material would include an inherent viscosity of 1.20, a K-Value of 77.0, a degree of polymerization of 1750, a North fineness of 5.00, and a specific gravity of 1.40.

The polymer is typically added to the composition at a concentration of at least 40 wt. %, in some embodiments at least 50 wt. %, in some embodiments at least 60 wt. %, in other embodiments at least 65 wt. %, based on the total weight of the composition. Typically, the polymer concentration is not greater than 80 wt. %, in some embodiments no greater than 75 wt. %, and in some embodiments preferably no greater than 70 wt. %. Polymer concentrations greater than 70 wt. % may be result in insufficient flexibility for certain medical applications (e.g., stethoscope tubing).

In other implementations, polyvinylchloride can be mixed with a variety of other polymers such as ethylene copolymers (e.g., ethylene—vinyl acetate copolymers), halogenated polyolefins (chlorinated polyethylene CPE, chlorosulfonated polyethylene), elastomers such as acrylonitrile-butadiene-styrene or methacrylate-butadiene—stryene, thermoplastic polyurethane elastomers (TPU's), polyester elastomers (Hytrel®, available from E. I. du Pont de Nemours & Co., Wilmington, Del.), and PVC graft polymers (PVC-EVA, PVC-PU).

Cationic Antimicrobial Agent

The cationic antimicrobial agent is a component of the composition that provides at least part of the antimicrobial activity. That is, the cationic antimicrobial agent has at least some antimicrobial activity for at least one microorganism. It is typically, in certain implementations, the main active component of the compositions described herein. The cationic antimicrobial agent includes an effective amount of one or more antimicrobial agents selected from the group consisting of biguanides and bisbiguanides such as chlorhexidine, alexidine, and their various salts including but not limited to the digluconate, diacetate, dimethosulfate, and dilactate salts, as well as combinations thereof; polymeric cationic ammonium compounds such as polyhexamethylenebiguanide salts; small molecule quaternary ammonium compounds such as benzalkonium halides; cationic antimicrobial dyes; and compatible combinations thereof.

Particularly useful cationic antimicrobial agents include benzalkonium chloride, chlorhexidine gluconate, octenidine dihydrochloride, cetyl pyridinium chloride, cetrimonium bromide, benzethonium chloride, polyhexamethylene biguanide salt, methylene blue, toluidiene blue, cationic dyes and compatible combinations thereof.

The cationic antimicrobial agent is typically added to the composition at a concentration of at least 0.05 wt. %, in some embodiments at least 0.1 wt. %, in some embodiments at least 0.2 wt. %, in some embodiments at least 0.5 wt. %, in some embodiments at least 1.0 wt. %, in other embodiments at least 2.0 wt. %, in yet other embodiments at least 3.0 wt. % and in yet other implementations at least 5.0 wt. %, in some cases exceeding 10 wt. %., based on the total weight of the composition. Preferably, the concentration is not greater than 25 wt. %, more preferably no greater than 20 wt. %, and most preferably no greater than 15 wt. %. A suitable range for cationic antimicrobial agent concentration to enhance active kill is at least 0.5 wt. % and no greater than 4.0 wt. %, based on the total weigh of the composition. It should be appreciated that the above concentrations relate to the total amount of cationic agent in the composition, even if a plurality of cationic antimicrobial agents are used.

Three classes of cationic antimicrobial agents suitable for the compositions of the present disclosure are discussed further below.

Biguanides

This class of antimicrobials is represented by the formula:

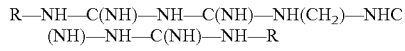

Where n=3-10, preferably 4-8, and most preferably 6; and R=$C_4$-$C_{18}$ branched or straight chain alkyl optionally substituted in available positions by halogen or $C_6$-$C_{12}$ aryl or alkaryl optionally substituted in available positions by halogen.

A particularly suitable compound of this class is chlorhexidine. This may be present as the free base but is preferably present as a disalt of acetate, gluconate, lactate, methosulfate ($CH_3OSO_3^-$), short chain or long chain fatty acids, a halide, or combinations thereof. The most preferred compound is chlorhexidine digluconate (CHG).

Polymeric Cationic Amine Compounds

Antimicrobial polymers comprising cationic amine groups may also be used as the cationic antimicrobial agent in the compositions described herein. These are typically polymers having quaternary amine groups with at least one alkyl or aralkyl chain of at least 6 carbon atoms and preferably as least 8 carbon atoms. The polymers may be linear, branched, hyperbranched or dendrimers. Suitable antimicrobial polymeric quaternary amine polymers may include those described in U.S. Pat. Nos. 6,440,405; 5,408,022; and 5,084,096; and International Publication No. WO/02102244.

Certain polybiguanides may be useful as cationic antimicrobial agents in the present compositions. Compounds of this class are represented by the formula:

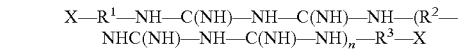

Where $R^1$, $R^2$, and $R^3$ are bridging groups such as polymethylene groups preferably having 2 to 10 methylene groups, more preferably 4 to 8 methylene groups and most preferably 6 methylene groups and where n equals 1 to 30 and is typically 4 to 12. The methylene groups can be optionally substituted in available positions with halogen, hydroxyl, or phenyl groups. X is a terminal group and is typically an amine, amine salt, or a dicyandiamide group. A particularly useful compound of this class is polyhexamethylene biguanide (PHMB) commercially available as Cosmocil CQ from Lonza Inc. South Plainfield, N.J.

Small Molecule Quaternary Ammonium Compounds

This class of compounds typically comprise one or more quaternary ammonium groups wherein attached to the quaternary ammonium group is at least one $C_6$-$C_{18}$ linear or branched alkyl or aralkyl chain. Suitable compounds include those disclosed in *Disinfection, Sterilization and Preservation*, S. Block, 4$^{th}$ ed., 1991, Chapter 13, Lea & Febiger. Particularly preferred compounds of this class have one or two $C_8$-$C_{18}$ alkyl or aralkyl chains bonded to at least one cationic nitrogen atoms and may be represented by the following formula:

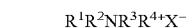

Where $R^1$ and $R^2$ are C1-C18 linear or branched alkyl, alkaryl, or aralkyl chains that may be substituted in available positions by N, O, or S provided at least one $R^1$ or $R^2$ is a $C_8$-$C_{18}$ linear or branched alkyl, alkaryl, or aralkyl chains that may be substituted in available positions by N, O, or S. $R^3$ and $R^4$ are $C_1$-$C_6$ alkyl, phenyl, benzyl, or $C_8$-$C_{12}$ alkaryl groups. $R^3$ and $R^4$ may also form a ring such as a pyridine ring with the nitrogen of the quaternary ammonium group. One or more R1-R4 may contain a bridging group to one or more additional nitrogen atoms. X is an anion, preferably a halide, and most preferably $C_1$— or Br—. Other anions may include methosulfate, ethosulfate, phosphates and the like. Suitable compounds of this class include monalyltrimethylammonium salts, monalkyldimethylbenzyl ammonium salts, dialkyldimethyl ammonium salts, benzethonium chloride. Also possible are cationic amines having cyclic amine groups such as those found in octenidine and hexitidine.

Examples of suitable quaternary ammonium antiseptics include benzalkonium halides having an alkyl chain length of $C_8$-$C_{18}$, more preferably $C_{12}$-$C_{16}$, and most preferably a mixture of chain lengths. For example, a typical benzalkonium chloride sample may be comprise of 40% $C_{12}$ alkyl chains, 50% $C_{14}$ alkyl chains, and 10% $C_{16}$ alkyl chains. These are commercially available from numerous sources including Lonza (Barquat MB-50); Benzalkonium halides substituted with alkyl groups on the phenyl ring. A commercially available example is Barquat 4250 available from Lonza; dimethyldialkylammonium halides where the alkyl groups have chain lengths of $C_8$-$C_{18}$. A mixture of chain lengths such as mixture of dioctyl, dilauryl, and dioctadecyl may be useful. Exemplary compounds are commercially available from Lonza as Bardac 2050, 205M and 2250 from Lonza; Cetylpyridinium halides such as cetylpyridinium chloride available from Merrell labs as Cepacol Chloride; Benzethonium halides and alkyl substituted benzethonium halides such as Hyamine 1622 and Hyamine 10× available from Rohm and Haas; octenidine and the like.

Vehicle

The vehicle of the hardenable antimicrobial compositions includes at least a plasticizer and a heat stabilizer package. The plasticizer is preferably selected to that is suitable for use with the polyhaloolefin homopolymer or copolymer. Particularly useful plasticizers and plasticizer blends are those that allow formation of PVC plastisols which harden when heated to elevated temperature. The heat stabilizer package may comprise one or more heat stabilizing elements, and typically comprises a zinc dialkyl carboxylate salts such as zinc dioctoate (often called zinc octoate). Components and concentrations of the vehicle are typically selected such that the cationic antimicrobial agent is at least partially soluble therein. In certain embodiments, the components of the vehicle are selected such that the cationic antimicrobial is substantially or completely soluble therein.

In particularly useful implementations, the cationic antimicrobial agent is at least partially soluble in the vehicle. In certain aspects, the cationic antimicrobial agent is dissolved or dispersed in the vehicle to a concentration of at least 0.2 wt. %, in some embodiments at least 0.3 wt-%, in some embodiments at least 0.5 wt. %, in some embodiments at least 0.75 wt. %, in other embodiments at least 1.0 wt. %, in yet other embodiments at least 2.0 wt. % and in yet other implementations at least 3.0 wt. %, based on the total weight of the vehicle. In certain desirable embodiments, the concentration of the dissolved or dispersed cationic antimicrobial agent is at least 0.75 wt. %, based on the total weight of the vehicle.

Plasticizer

Plasticizers that may be added to the composition of the present disclosure may be selected from a wide variety of commercially available materials. In each case, the added plasticizer should preferably be compatible with the polyhaloolefin (typically PVC) resin used in the formulation. By "compatible" it is meant that the plasticizer is capable of plasticizing the polyhaloolefin and thus decreasing the glass transition temperature of the plasticizer/polyhaloolefin composition relative to that of the polymer alone. Preferred plasticizers are stable at the concentration used and do not result in substantial free plasticizer at the surface, which can appear as an oily residue. Plasticizers are typically selected such that they are not easily substantially extracted in either organic or aqueous solutions (including those with aqueous buffers), i.e., extraction is minimal and is considered acceptable by those skilled in the art. Representative plasticizers include: di-2-ethylhexyl phthalate (DOP), diisooctyl phthalate (DIOP), branched C9 phthalates (Jayflex DINP type-moderate branching); strong solvating plasticizers including disobutyl phthalate, dibutyl phthalate (DBP), butyl benzyl phthalate (BBP), benzoates, alkyl sulfonates (MESAMOLL); low volatility plasticizers such as trimellitates (Tris-2-ethylhexyl trimellitate (TOTM), diisodecyl phthalate (DIDP), epoxy plasticizers, polymeric plasticizers, and low temperature plasticizers such as phthalates of straight chain and linear alcohols; GRINSTED SOFT-N-SAFE plasticizer, available from Danisco A/S, Denmark; and compatible combinations thereof. Particularly useful plasticizers include acetyl tributyl citrate, trioctyl trimellitate, dioctyl adipate, polyester adipate, 1,2-cyclohexane dicarboxylic acid diisononyl ester (available as HEXAMOLL DINCH, from BASF), MESAMOLL, dipropynl glycol dibenzoate, and combinations thereof.

The amount of plasticizer used can vary depending on the desired flexibility of the article component created from the composition. The plasticizer is typically added to the composition at a concentration of at least 10 wt. %, in some embodiments at least 20 wt. %, in some embodiments at least 30 wt. %, in other embodiments at least 40 wt. %, based on the total weight of the composition. Preferably, the concentration is not greater than 65 wt. %, ion some embodiments not greater than 60 wt. %, and in other embodiments not greater than 50 wt. %, based on the total weight of the composition.

Heat Stabilizer Package

The heat stabilizer package typically includes one or more heat stabilizing compounds, including primary heat stabilizers and secondary heat stabilizers. As used herein, "heat stabilizers" are compounds that are capable of providing thermal stability to polyhaloolefin compositions during high temperature processing. High temperatures include temperatures of at least 200 degrees Fahrenheit (F), in some embodiments at least 250 degrees F., in some implementations, at least 300 degrees F., and in some implementations at least 325 degrees F. In some implementations, the heat stabilizer package includes a plurality of primary heat stabilizers, and in yet other implementation, the packages includes one or more secondary heat stabilizers. In certain particularly suitable embodiments, the heat stabilizer package includes zinc octoate and at least one secondary heat stabilizer.

Representative primary heat stabilizers includes zinc, tin, calcium, barium, strontium, and magnesium salts, the anions of which originate from aliphatic monocarboxylic acid or dicarboxylic acids having 2 to 24 carbon atoms (which may or may not be saturated), or from monoalkyl esters, or monoalkenyl esters of the above aliphatic dicarboxylic acids, or from aromatic or alicyclic monocarboxylic acid (which may or may not be substituted). Further exemplary anions are those derived from maleic, acetic, diacetic, propionic, hexanoic, 2-ethylhexanoic, octanoic, decanoic, undecanoic, lauric, myristic, palmitic, stearic, oleic, ricinoleic, behenic, hydroxystearic, hydroxyundecanoic, benzoic, phenylacetic, alkylbenzoic, para-tert-butylbenzoic, and salicylic acids. Further exemplary primary heat stabilizers include aromatic monocarboxylic acids such as benzoic acid, p-tert-butylbenzoic acid, dimethylhydroxybenzoic acid, 3,5-di-tert-butyl-4-hydroxybenzoic acid, toluic acid, dimethylbenzoic acid, ethylbenzoic acid, n-propylbenzoic acid, salicylic acid, p-tert-octylsalicylic acid, and aromatic dicarboxylic acids such as phthalic acid, isophthalic acid, terephthalic acid and hydroxyphthalic acid; and aromatic polycarboxylic acids such as hemimellitic acid, trimellitic acid, pyromellitic acid, as well as aralkyl carboxylic acids such as mandelic acid.

Particularly useful primary heat stabilizers include zinc salts such as zinc dioctoate (i.e., zinc caprylate, zinc octoate, zinc 2-ethylhexanoate, and zinoctanoate), calcium dioctoate, and other mixed metal stabilizers including cadmium, barium, zinc and calcium. Salts of quaternary amines can also be used.

Representative secondary heat stabilizers include epoxides, particularly epoxidized polyglycerides, including but not limited to epoxidized soy bean oil, epoxidized linseed oil, epoxidized fish oil or tall oil, epoxidized fatty acid esters, and other epoxidized hydrocarbons. Additional heat stabilizing elements may also be added to the heat stabilizer package, including alkyl or aryl phosphites known for their stabilizing activity, such as phenyl-2-ethylhexyl phosphite, triisodecyl phosphite, tris(nonylphenyl)phosphite, and diisooctyl pentaerthryityl diphosphite. Other heat stabilizers include organometallic stabilizers including dialkyltin dicarboxylates (e.g., dibutyltin dilaurate, dioctyltinmaleate, dimethyltin bis (isooctyl mercaptoacetate, and dibutyltin bis(2-mercaptoethyl oleate). Phenolic compounds such as hindered phenol antioxidants such as butyl hydroxytoluene (BHT), butylated hydroxyaniosole (BHA) and the like may also be used as part of the heat stabilizer package.

The heat stabilizer package is typically added to the composition at a concentration of at least 1.0 wt. %, in some embodiments at least 2.0 wt. %, in some embodiments at least 3.0 wt. %, in other embodiments at least 4.0 wt. %, based on the total weight of the composition. Preferably, the concentration is not greater than 15.0 wt. %, in some embodiments not greater than 10.0 wt. %, and in other embodiments not greater than 9.0 wt. %, based on the total weight of the composition.

When used, a primary heat stabilizer is typically added to the composition at a concentration of at least 0.5 wt. %, in some embodiments at least 1.0 wt. %, in some embodiments at least 2.0 wt. %, based on the total weight of the composition. Preferably, the concentration of primary heat stabilizer is not greater than 7.0 wt. %, in some embodiments not greater than 6.0 wt. %, and in other embodiments not greater than 5.0 wt. %, based on the total weight of the composition.

An optimal amount of antimicrobial efficacy and degradation reduction typically occurs with increasing addition of the primary heat stabilizer relative to the cationic antimicrobial agent. In certain implementations, the weight ratio of concentration of the primary heat stabilizer to the cationic antimicrobial agent is at least 1:1; in some embodiments 2:1, and in yet other embodiments 3:1. Without wishing to be bound by theory, a cationic antimicrobial agent renders heat stabilization of polyvinyl chloride more difficult, requiring additional primary heat stabilizer to counteract this effect. It is likely, therefore, that adding an effective amount of cationic antimicrobial agent to a plastisol or resin that includes only a typical concentration of heat stabilizer(s) will result in degradation of the resin, the agent, or both.

Optional Additives

The antimicrobial compositions of the present disclosure may also feature one or more secondary antimicrobials, a surfactant, and an organic solvent. Other optional additives include antistatic agents, air release agents, mold release agents, antiblocking agents, dispersing agents, degassing agents, viscosity modifiers, flame retardants, antioxidants, antifog agents, gloss enhancers, colorants, lubricant, uv light stabilizers, pigments, dyes and fillers could be used to prepare the hardened composition. These optional additives may, in some implementations, impart additional antimicrobial activity to the hardened composition and/or further improve the solubility of the cationic antimicrobial agent.

Secondary Antimicrobials

Additional secondary antimicrobial agents may be added to the hardenable composition, so long as they are compatible with the remaining components (e.g., the components of the hardenable composition filling do not substantially prevent the activity of the antimicrobial agent; the antimicrobial agent does not result in degradation of the polymer). Exemplary secondary antimicrobials include phenolic antiseptics such as parachlorometaxylenol (PCMX), triclosan, hexachlorophene, and others disclosed in U.S. Pat. No. 8,198,326 (Scholz); fatty acid monoesters of glycerin and propylene glycol such as glycerol monolaurate, glycerol monocaprylate, glycerol monocaprate, propylene glycol monolaurate, propylene glycol monocaprylate, propylene glycol moncaprate, $C_8$-$C_{12}$ alkyl monoethers of glycerin and propylene glycol such as 2-ethylhexyl glycerin ether (available from Schuelke Mayr, Norderstedt, Germany, under the trade designation "SENSIVA SC 50") as well as other antimicrobial lipids disclosed in U.S. patent application Ser. No. 10/659,571, which is incorporated herein by reference in its entirety; natural oil antiseptics disclosed in U.S. Patent Publication No. 2006/0051384 (Scholz et al.); $C_6$-$C_{12}$ alkyl and aryl carboxylic acids; quaternary silanes, silver, silver salts such as silver chloride, silver oxide silver sulfadiazine, copper, copper salts, and combinations thereof.

Various combinations of antimicrobial agents can be used in the compositions of the present disclosure. Suitable antiseptics include, for example: antimicrobial lipids; phenolic antiseptics; cationic antiseptics; iodophors; antimicrobial natural oils; or combinations thereof.

The composition may also include certain biocides typically used in the industry to kill/inhibit bacteria, fungi or algae. These can include, but are not limited to, biocides such as 10,10'-Oxybisphenylarsine (OBPA), N Trichloromethylmercaptophthalimide (Folpet), 2-n-Octyl-4-isothiazoline-3-one (octhilinone), N-Trichloromethylmercatotetrahydrophthalimide (Captan).

Surfactants

The hardened antimicrobial composition of the present disclosure may further include a nonionic, zwitterionic, or cationic surfactant. Certain surfactants may further enhance the solubility of the cationic antimicrobial in the vehicle, thereby enhancing resistance to degradation during cure and subsequent availability at the surface. The surfactants are preferably compatible with the cationic antimicrobial agent, the polymer, and plasticizer/heat stabilizer vehicle, as well as any other optional ingredients, such as the organic solvent. In addition, certain surfactants may increase the antimicrobial activity. Non-ionic surfactants are particularly suitable for inclusion in the antimicrobial compositions of the present inventions.

Exemplary nonionic surfactants include, but are not limited to, alkyl glucosides, alkyl polyglucosides, polyhydroxy fatty acid amides, sucrose esters, esters of fatty acids and polyhydric alcohols, fatty acid alkanolamides, ethoxylated fatty acids, ethoxylated aliphatic acids, ethoxylated fatty alcohols (e.g., octyl phenoxy polyethoxyethanol available under the trade name TRITON and nonyl phenoxy poly(ethyleneoxy) ethanol available under the trade name NONIDET, both from Sigma, St. Louis, Mo.), ethoxylated and/or propoxylated aliphatic alcohols (e.g., that available under the trade name Brij from ICI), ethoxylated glycerides, ethoxylated/propoxylated block copolymers such as the Pluronic and Tetronic surfactants available from BASF, ethoxylated cyclic ether adducts, ethoxylated amide and imidazoline adducts, ethoxylated amine adducts, ethoxylated mercaptan adducts, ethoxylated condensates with alkyl phenols, ethoxylated nitrogen-based hydrophobes, ethoxylated polyoxypropylenes, polymeric silicones, fluorinated surfactants (e.g., those available under the trade names FLUORAD, 3M Company, St. Paul, Minn., and ZONYL from Dupont de Nemours Co., Wilmington, Del.), polyglycerylesters of fatty acids such as those sold by Abitec Janesville Wis. under the Caprol tradename (e.g., polyglyceryl 10 decastearate), and polymerizable (reactive) surfactants (e.g., SAM 211 (alkylene polyalkoxy sulfate) surfactant available under the trade name MAZON from PPG Industries, Inc., Pittsburgh, Pa.).

Exemplary cationic surfactants include dimethyl disteryl ammonium chloride, behenyl trimethyl ammonium methosulfate (available from Croda USA). Exemplary zwitterionic surfactants include, but are not limited to, betaine and sultaine.

Organic Solvents

The composition of the present disclosure may further comprise an organic solvent. Without wishing to be bound by theory, certain organic solvents may further increase the solubility of the cationic antimicrobial in the vehicle. In certain implementations, suitable organic solvents include small molecule solvents. Exemplary small molecule organic solvents include, but are not limited to, benzyl alcohol, 1, 2 hexylene glycol, and phenoxy ethanol. Typically, if present, the lower boiling, more volatile components are limited to less than 10% by weight of the hardened composition. Certain organic solvents, including those exemplified above, may impart additional antimicrobial activity.

Methods of Preparation

The present disclosure also provides methods for preparing a hardenable, antimicrobial composition. The method includes providing a vehicle including a plasticizer and a heat stabilizer. The method may include a obtaining a premixed vehicle or the additional step of admixing the heat stabilizer package and the plasticizer. One of the plasticizer and the heat stabilizer package may include an organic solvent, in some implementations. Next, the method includes providing a cationic antimicrobial agent. The agent may be mixed with the vehicle, or may be set aside until a later time. If admixed with the vehicle, the resulting composition may be analyzed (visually or quantitatively) for solubility of the antimicrobial agent.

Next, a polyhaloolefin polymer composition may be obtained, which typically includes at least one polyvinyl chloride polymer (including homopolymers and copolymers). Additional components, including but not limited to secondary antimicrobials, solvents, surfactants, and other additives (e.g., octanoic acid) to facilitate processing or mixing may be added at any point in the mixing process. The vehicle, the cationic antimicrobial, the polymer, and any other additives may be mixed to create a hardenable composition. The mixture is typically allowed to settle prior to hardening. Persons skilled in the art will understand that the selection of process parameters will vary based on the components of the composition and the desired features of the article to be formed.

Exemplary Articles

As nonlimiting examples, compositions of the disclosure may be used for fabrication of catheters, gloves, stethoscope tubing, grips, sleeves, insulators and other dipped products by standard form dipping methods, and polyvinyl plastisols according to the present disclosure can provide dippable and castable antimicrobial polyvinyl chloride devices. Thus, the final article can be formed from one or more of the compositions of the present disclosure. In such implementations, the cationic antimicrobial agent will be distributed throughout the polymer matrix. The distribution may be uniform or non-uniform, but will typically be present at all layers of the article formed from the antimicrobial composition. The presence of antimicrobial agent throughout the polymer matrix can, without wishing to be bound by theory, prolong the antimicrobial activity by replenishing or regenerating the antimicrobial agent at the surface.

Alternatively, compositions of the invention can be formulated into high solids coating compositions that can be used to dip-fabricate a variety of medical devices, such as catheters, stents, gloves, condoms, and the like.

By another method, compositions of the invention can be dried and melt processed, for example, by injection molding and extrusion. Compositions used for this method can be used alone or compounded with any other melt-processable material for molding and extrusion of antimicrobial articles.

If used as a coating, the compositions can be applied by any means, including those methods known in the art. For example, the compositions can be brushed or sprayed onto the article, or the article can be dipped into the composition. For example, the article can be dipped into the antimicrobial polymer solution at a rate of about 10-80 inches per minute (ipm), preferably about 40 ipm. In certain processes, the article can be heated to an elevated temperature prior to being dipped into the composition. The article is allowed to remain in the antimicrobial polymer solution for a period of about 0-30 seconds, preferably about 5-15 seconds. The article is then withdrawn at a rate of about 10-80 ipm, preferably about 15-30 ipm. Once the article has been coated with the hardenable polyhaloolefin composition of the disclosure, it is allowed to air dry for a period of at least about 10 minutes before drying is completed in an oven for a period of about 5-60 minutes at a temperature in the range of about 40-100° C. Preferably, oven drying occurs for a period of about 15 minutes at a temperature of about 50° C. The coated article can optionally be dried with a hot air stream at a temperature in the range of approximately 40° C. to approximately 100° C. for a period of about 5-60 minutes to remove residual solvent. Persons skilled in the art will understand that the parameters in the foregoing paragraph are merely examples and will vary based on the composition of the substrate and coating and the desired features of the coated objects.

Certain fabrication techniques, particularly dip coating, allow for multiple layers of hardened polyhaloolefin composition to be formed. Thicker regions of the article (e.g., those having multiple layers) may have a greater concentration of antimicrobial agent incorporated therein and/or available at the surface.

Once prepared according the methods described above, the antimicrobial composition of the present disclosure may be used to create a component of a stethoscope. In some embodiments, the hardenable antimicrobial composition is suitable for use in conjunction with a mechanical stethoscope. A typical mechanical stethoscope includes a sound receiving member or chestpiece connected to tubing which divides at a yoke into a headset having dual sound transmitting tubes and terminating in ear tips. The lower end of the tubing is typically adapted to be coupled to a stem fitting extending from the chestpiece. In certain implementations, at least a portion of the tubing is formed from an antimicrobial, polyhaloolefin composition of the presentation disclosure. In certain particularly useful implementations, all or nearly all of the tubing may be formed from an antimicrobial composition of the present disclosure.

Methods for creating stethoscope binaural tubing from a plastisol are known and include those described in U.S. Pat. Nos. 5,111,904; 5,380,182; and 5,324,471, all to Packard et al.

The hardenable antimicrobial compositions are likewise suitable for use in conjunction with an electronic stethoscope. An electronic stethoscope typically includes ear tips, ear tubes, and a main tube. The main tube is coupled to a main housing or chestpiece, which supports one or more sensors. The signal processing circuitry of the electronic stethoscope typically includes a digital filter and other optional circuitry. The signal processing circuitry is configured to convert the signals generated by the sensor to acoustic signals for transmission through the ear tubes to reproduce body sounds through the ear tips. In certain implementations, at least a portion of the main tube is formed from an antimicrobial, polyhaloolefin composition of the presentation disclosure. In certain particularly useful implementations, the entire main tube may be formed from an antimicrobial composition of the present disclosure. Exemplary electronic stethoscope constructions may be found, for example, in U.S. Publication No. 2011/0190665.

Additional useful medical articles that can be formed with the antimicrobial compositions include, but are not limited to: nasal gastric tubes, blood stream catheters, dialysis catheters and tubing stents, surgical tools, tympanoplasty tubes, shunts including shunts for hydrocephalus, post surgical drain tubes and drain devices, urinary catheters, endotraecheal tubes, other implantable devices, and other indwelling devices.

Objects and advantages of this invention are further illustrated by the following examples, but the particular materials and amounts thereof recited in these examples, as well as other conditions and details, should not be construed to unduly limit this invention. Unless otherwise indicated, all parts and percentages are by weight.

EXAMPLES

TABLE 1A

Antimicrobial Chemicals used in Examples.

| Chemical | Common Name/ Synonym/Abbreviation | Manufacturer; Location |
|---|---|---|
| Benzethonium chloride | BZT | Sigma Aldrich; St. Louis, MO (USA) |
| Benzyl dimethyl tetradecyl ammonium chloride | BKC; Benzalkonium Chloride, | Dishman Pharmaceuticals and Chemicals Limited; Ahmedabad (India) |
| Cetylpyridinium Chloride monohydrate form | CPC | Sigma Aldrich; St. Louis, MO (USA) |
| Octanoic Acid | 2-ethylhexanoic acid, | Alfa Aesar; Ward Hill, MA (USA) |
| Octenidine dihydrochloride | OCT | Dishman Pharmaceuticals and Chemicals Limited; Ahmedabad (India) |
| Parachlorometaxylenol | PCMX, OTTASEPT | Jiangsu Huanxin High-Tech Materials Co., Ltd.; Jiangsu, (China) |
| Polyhexamethylene biguanide | PHMB, Cosmocil 100 | Arch UK Biocides LTD (Lonza); Castleford (UK) |
| 2-phenoxyethanol | POEtOH | Alfa Aesar; Ward Hill, MA (USA |

TABLE 1B

Plasticizer Chemicals used in Examples.

| Chemical | Common Name/ Synonym/Abbreviation | Manufacturer; Location |
|---|---|---|
| Acetyl Tributyl Citrate | ATC; Citroflex A4 | Morflex Inc.; Greensboro, NC (USA) |
| BENZOFLEX VP-953; or 2088; or 9-88 | benzoate ester | Eastman Chemical Company, Kingsport, TN (USA) |
| Butylbenzyl phthalate | BBP; PLASTHALL BBP | Hallstar Company; Chicago, IL (USA) |
| 1,2-cyclohexanedicarboxylic acid diisononyl ester | HEXAMOLL DINCH, DINCH | BASF; Ludwigshafen (Germany) |

TABLE 1B-continued

Plasticizer Chemicals used in Examples.

| Chemical | Common Name/Synonym/Abbreviation | Manufacturer; Location |
|---|---|---|
| Dipropylene glycol dibenzoate (98%) | DPGDB | Sigma Aldrich; St. Louis, MO (USA) |
| Dioctyl Adipate | DOA, PLASTHALL DOA | Hallstar Company; Chicago, IL (USA) |
| Di(2-ethylhexyl) phthalate | DEHP; PLASTHALL DOP | Hallstar Company; Chicago, IL (USA) |
| MESAMOLL or MESAMOLL II | an alkylsulphonic acid ester with phenol | LanXess, Singapore |
| Di-ethylhexyl ester (>96%) and Ethylhexyl methyl ester (<3%) | EASTMAN 168; non-phthalate plasticizer | Eastman Chemical Company, Kingsport, TN (USA) |
| Polyester adipate | PLASTHALL P-643; PEA | Hallstar Company; Chicago, IL (USA |
| Trioctyl Trimellitate | TOTM; Tris(2-ethylhexyl)benzene-1,2,4-tricarboxylate | OXEA Corp.; Oberhausen (Germany) |

TABLE 1C

Heat Stabilizer Chemicals used in Examples.

| Chemical | Common Name/Synonym/Abbreviation | Manufacturer; Location |
|---|---|---|
| Decyl diphenyl phosphite | DDPP | Hooker Industrial Chemicals Div.; Niagara Falls, NY (USA) |
| Diisodecyl phenyl phosphite | di-IDPP | Borg Warner Chemicals; Auburn Hills, MI (USA) |
| Epoxidized soybean oil | ESO | AK Scientific, Inc.; Union City, CA (USA) |
| Triisodecyl phosphite | TIDP; phosphorous acid triisodecyl ester | TCI (Tokyo Chemical Company) America; Portland, Oregon (USA) |
| Tris(nonylphenyl) phosphite, | TNPP | Sigma Aldrich; St. Louis, MO (USA) |
| Zinc 2-ethylhexanoate, Zn 22% Cont. 1% diethylene glycol | Zinc octoate, ZnOct | Alfa Aesar; Ward Hill, MA (USA) |

All formulation components are reported in percent weight/weight (% wt/wt) unless otherwise noted.

Example 1

The solubility of three different antimicrobial agents: benzalkonium chloride (BKC), octenidine dihydrochloride (OCT), and polyhexamethylene biguanide (PHMB); in various plasticizers was evaluated by the following procedure. The antimicrobial agent was added to a small vial; to this, the plasticizer of interest was added. The solution was allowed to roll for 16 hours at 60 rpm in order to determine if the antimicrobial was soluble in that system. In each solution, 1.5% wt/wt of one antimicrobial agent (BKC, OCT, or PHMB) was combined with 98.5% wt/wt of one of each of the following plasticizers: DINCH, acetyl tributyl citrate, trioctyl trimellitate, dioctyl adipate, or polyester adipate. In each case, none of these antimicrobial agents were soluble in any of these plasticizers at the concentrations evaluated.

Example 2

Example 2 was performed to determine if the solubility of BKC, OCT, and PHMB in various plasticizers are influenced by the presence of the heat stabilizer package which may be used in a flexible polyvinyl chloride (FPVC) formulation. To the vial containing the plasticizer and antimicrobial, the appropriate amount (see below) of a master batch solution of PVC heat stabilizer was added. The master batch solution of PVC heat stabilizer included: epoxidized soybean oil (ESO), decyl diphenyl Phosphite (DDPP), and zinc octoate (ZnOct). The solution was allowed to roll overnight at ambient temperature at 60 rpm to determine if the antimicrobial was soluble in that system. Samples were evaluated visually for solubility. The diameter of the vial through which optical clarity (i.e., solubility) was assessed was approximately 2.5 cm. Samples that were clear were judged to have the cationic antimicrobial completely soluble. Those that were hazy were judged to have the antimicrobial partially soluble. Those that were opaque white were substantially insoluble.

TABLE 2A

| Components | Ex. 2-1 | Ex. 2-2 | Ex. 2-3 | Ex. 2-4 | Ex. 2-5 |
|---|---|---|---|---|---|
| BKC | 1.1 | 1.1 | 1.1 | 1.1 | 1.1 |
| DINCH | 70.8 | 0 | 0 | 0 | 0 |
| ATC | 0 | 70.6 | 0 | 0 | 0 |
| TOTM | 0 | 0 | 70.7 | 0 | 0 |
| DOA | 0 | 0 | 0 | 70.7 | 0 |
| PEA | 0 | 0 | 0 | 0 | 70.8 |
| ESO | 15.6 | 15.7 | 15.6 | 15.6 | 15.6 |
| DDPP | 8.9 | 9.0 | 9.0 | 9.0 | 8.9 |
| ZnOct | 3.6 | 3.6 | 3.6 | 3.6 | 3.6 |
| Total Wt. % | 100.0 | 100.0 | 100.0 | 100.0 | 100.0 |
| Solubility | Soluble | Soluble | Semi Soluble; | Soluble | Semi-Soluble |

TABLE 2A-continued

| Components | Ex. 2-1 | Ex. 2-2 | Ex. 2-3 | Ex. 2-4 | Ex. 2-5 |
|---|---|---|---|---|---|
| Solution Appearance | clear/ colorless | clear/light yellow | clear/ colorless with some white solid | clear/ colorless | clear/ colorless with some white solid |

TABLE 2B

| Components | Ex. 2-6 | Ex. 2-7 | Ex. 2-8 | Ex. 2-9 | Ex. 2-10 |
|---|---|---|---|---|---|
| OCT | 1.1 | 1.1 | 1.1 | 1.1 | 1.1 |
| DINCH | 70.7 | 0 | 0 | 0 | 0 |
| ATC | 0 | 70.6 | 0 | 0 | 0 |
| TOTM | 0 | 0 | 70.7 | 0 | 0 |
| DOA | 0 | 0 | 0 | 70.6 | 0 |
| PEA | 0 | 0 | 0 | 0 | 70.6 |
| ESO | 15.6 | 15.7 | 15.6 | 15.7 | 15.7 |
| DDPP | 9.0 | 9.0 | 9.0 | 9.0 | 9.0 |
| ZnOct | 3.6 | 3.6 | 3.6 | 3.6 | 3.6 |
| Total Wt. % | 100.0 | 100.0 | 100.00 | 100.0 | 100.0 |
| Solubility | Insoluble | Insoluble | Insoluble | Insoluble | Insoluble |

TABLE 2C

| Components | Ex. 2-11 | Ex. 2-12 | Ex. 2-13 | Ex. 2-14 | Ex. 2-15 |
|---|---|---|---|---|---|
| PHMB | 1.1 | 1.1 | 1.1 | 1.1 | 1.1 |
| DINCH | 70.6 | 0 | 0 | 0 | 0 |
| ATC | 0 | 70.6 | 0 | 0 | 0 |
| TOTM | 0 | 0 | 70.7 | 0 | 0 |
| DOA | 0 | 0 | 0 | 70.6 | 0 |
| PEA | 0 | 0 | 0 | 0 | 70.7 |
| ESO | 15.7 | 15.7 | 15.6 | 15.7 | 15.6 |
| DDPP | 9.0 | 9.0 | 9.0 | 9.0 | 9.0 |
| ZnOct | 3.6 | 3.6 | 3.6 | 3.6 | 3.6 |
| Total Wt. % | 100.0 | 100.0 | 100.0 | 100.0 | 100.0 |
| Solubility | Insoluble | Insoluble | Insoluble | Insoluble | Insoluble |

The results of Example 2 showed that 1.1 wt % benzalkonium chloride (BKC) is soluble in DINCH, acetyl tributyl citrate (ATC), trioctyl trimellitate (TOTM), dioctyl adipate (DOA), and polyester adipate (PEA), as long as there is a heat stabilizing package (ESO, DDPP and ZnOct) present in solution. Octenidine dihydrochloride (OCT) and PHMB at 1.1 wt % are not soluble in DINCH, ATC, TOTM, DOA, and PEA, even if there is a heat stabilizing package present.

Example 3

Example 3 was performed to evaluate the stability of cationic antimicrobials in flexible PVC (FPVC) formulations with increasing amounts of the primary heat stabilizer (ZnOct).

The antimicrobial agent was added to a small vial. For samples containing CPC or OCT, benzyl alcohol (BzOH, available from Mallinkrodt Baker Inc. of Phillipsburg, N.J.), was also added and the mixture was vortexed. Zinc octoate (ZnOct) was then added to the mixture. In a separate jar, a batch mixture containing DINCH, ESO and di-IDPP was prepared; the solution was allowed to roll until a clear/colorless mixture was obtained with no mixing lines. In a separate jar, the appropriate amount of batch mixture was added into the vial containing the antimicrobial agent, solvent, and zinc octoate (ZnOct). The mixture was vortexed and the solution was allowed to roll at a setting of 60 rpm until a determination was made as to whether or not the antimicrobial was dissolving in the solution.

Next, the mixture was vortexed and PVC resin (polyvinyl chloride homopolymer, GEON series PVC resin available from PolyOne Corp. of Avon Lake, Ohio (USA)) was added to the solution and mixed by hand. Hereafter, in the following Examples, this PVC resin will simply be referred to as PVC. The plastisol was allowed to roll overnight to swell the PVC. Then, 9 grams of each formulation was added to a 15 mL centrifuge tube. The samples were centrifuged at room temperature at 1500 rpm for 6 min to remove any air entrapped in the plastisol. The plastisol was dispensed into aluminum weigh dishes and cured at 177° C. (350° F.) for 10 minutes.

TABLE 3A

Controls - No Antimicrobial Agent

| Components | Ex. 3-1 | Ex. 3-2 | Ex. 3-3 | Ex. 3-4 | Ex. 3-5 | Ex. 3-6 |
|---|---|---|---|---|---|---|
| PVC | 48.2 | 47.9 | 47.8 | 47.2 | 46.7 | 46.5 |
| DINCH | 38.6 | 38.3 | 38.1 | 37.9 | 37.4 | 36.8 |
| ESO | 8.4 | 8.3 | 8.3 | 8.2 | 8.1 | 8.0 |
| di-IDPP | 4.8 | 4.8 | 4.8 | 4.7 | 4.7 | 4.6 |
| ZnOct | 0 | 0.7 | 1.0 | 2.0 | 3.1 | 4.1 |
| Total Wt. % | 100 | 100 | 100 | 100 | 100 | 100 |
| Cured Appearance | Clear Yellow | Clear colorless | Clear Colorless | Semi-Clear | Semi-Clear | Opaque White |

TABLE 3B

| Components | Ex. 3-7 | Ex. 3-8 | Ex. 3-9 | Ex. 3-10 | Ex. 3-11 | Ex. 3-12 |
|---|---|---|---|---|---|---|
| BKC | 1.5 | 1.5 | 1.5 | 1.5 | 1.5 | 1.5 |
| PVC | 47.3 | 47.2 | 47.1 | 46.8 | 46.1 | 45.6 |
| DINCH | 38.1 | 37.7 | 37.4 | 37.0 | 36.8 | 36.4 |
| ESO | 8.3 | 8.2 | 8.1 | 8.0 | 8.0 | 7.9 |
| di-IDPP | 4.8 | 4.7 | 4.7 | 4.6 | 4.6 | 4.6 |
| ZnOct | 0.0 | 0.6 | 1.2 | 2.1 | 3.0 | 4.0 |
| Total Wt. % | 100 | 100 | 100 | 100 | 100 | 100 |
| Cured Appearance | Clear Dark orange edges & mostly opaque black center | Mostly clear yellow with a few dark orange brown spots. | Clear light yellow, some small gas pockets | Clear almost colorless, very light yellow, some small gas pockets | Clear almost colorless, very light yellow with some opaque white, some small gas pockets | Clear almost colorless, very light yellow with more opaque white, some small gas pockets |

TABLE 3C

| Components | Ex. 3-13 | Ex. 3-14 | Ex. 3-15 | Ex. 3-16 | Ex. 3-17 | Ex. 3-18 |
|---|---|---|---|---|---|---|
| CPC | 1.5 | 1.5 | 1.5 | 1.5 | 1.5 | 1.5 |
| BzOH | 3.9 | 3.8 | 3.7 | 3.7 | 3.6 | 3.6 |
| PVC | 45.6 | 45.3 | 45.3 | 44.7 | 44.1 | 43.8 |
| DINCH | 36.5 | 36.4 | 36.1 | 35.7 | 35.4 | 35.0 |
| ESO | 7.9 | 7.9 | 7.9 | 7.8 | 7.7 | 7.6 |
| di-IDPP | 4.6 | 4.5 | 4.5 | 4.5 | 4.4 | 4.4 |
| ZnOct | 0 | 0.5 | 1.0 | 2.2 | 3.3 | 4.0 |
| Total Wt. % | 100 | 100 | 100 | 100 | 100 | 100 |
| Cured Appearance | Clear dark red | Clear dark orange | Clear dark orange | Clear dark orange | Clear lighter dark orange | Clear lighter dark orange |

TABLE 3D

| Components | Ex. 3-19 | Ex. 3-20 | Ex. 3-21 | Ex. 3-22 | Ex. 3-23 | Ex. 3-24 |
|---|---|---|---|---|---|---|
| OCT | 1.5 | 1.5 | 1.5 | 1.5 | 1.5 | 1.5 |
| BzOH | 7.2 | 7.1 | 7.1 | 7.1 | 7.0 | 6.7 |
| PVC | 44.2 | 43.9 | 43.6 | 43.1 | 42.8 | 42.3 |
| DINCH | 35.1 | 35.0 | 34.8 | 34.4 | 34.0 | 33.9 |
| ESO | 7.6 | 7.6 | 7.6 | 7.5 | 7.4 | 7.4 |
| di-IDPP | 4.4 | 4.4 | 4.4 | 4.3 | 4.3 | 4.2 |
| ZnOct | 0 | 0.5 | 1.0 | 2.1 | 3.1 | 4.0 |
| Total Wt. % | 100 | 100 | 100 | 100 | 100 | 100 |
| Cured Appearance | Opaque dark brown edges and semi-clear dark orange | Semi-clear yellow | Semi-clear very light yellow with one opaque spot | Semi-clear very light yellow | Semi-clear very light yellow | Semi-clear very light yellow |

The results of Example 3 indicate that the presence of the cationic antimicrobial increases the degradation of the PVC upon curing. The addition of a primary heat stabilizer, such as zinc octoate (ZnOct), inhibits this degradation. Zinc octoate also plays a role in the solubility of the cationic antimicrobial in the plastisol. As the amount of ZnOct was increased, so was the solubility of the antimicrobials.

Example 4

Example 4 evaluated the limits to the addition of both BKC and zinc octoate (ZnOct), which were varied from 0 to 4 weight percent of the total plastisol formulation. All samples were cured at 177° C. (350° F.) for 10 minutes The BKC was dispensed into a 25 mL vial. To this was added the DINCH, TIDP, and ZnOct in that order. The vial was then capped and vortexed for several seconds, and then placed on rollers set at 65 rpm in order to promote the dissolution (if possible) of the BKC. After rolling for several hours, the samples were uncapped, placed in an oven at 80° C. for five minutes, then removed, recapped and placed back on the rollers for an additional five minutes. The added step of placing the samples in the oven was to also expedite the dissolution of BKC. It was observed that as the content of BKC increased, the solutions had less clarity and were whiter in color. It was also observed that in the absence of ZnOct, there was much less solubility of the BKC.

Five grams of PVC resin was then added to each of the solutions. The solutions were then mixed vigorously by hand and allowed to roll overnight at 45 rpm to ensure thorough mixing. The samples were then dispensed into aluminum weigh dishes and cured at 177° C. (350° F.) for 10 minutes resulting in "pucks" of cured PVC.

The following abbreviations were used for the sample appearance observed of the cured "puck" of flexible PVC for Example 4 and 5: C=clear, O=opaque, Y=yellow, W=White, B=Black, F=film on surface, S=surface bumpy, g=small gas bubbles, G=large gas bubbles.

Note that a "puck" of cured material may have different regions with slightly different appearances and/or combinations of appearances within the same regions or the entirety of the "puck.". For example a cured PVC sample may have separate regions that are clear and somewhat opaque and thus be described as "C/O."

TABLE 4A

| Components | Ex. 4-1 | Ex. 4-2 | Ex. 4-3 | Ex. 4-4 | Ex. 4-5 |
|---|---|---|---|---|---|
| BKC | 0.0 | 0.0 | 0.0 | 0.0 | 0.0 |
| DINCH | 47.0 | 46.3 | 45.9 | 45.6 | 44.9 |
| PVC | 48.2 | 47.7 | 47.0 | 46.6 | 46.3 |
| TIDP | 4.8 | 4.9 | 4.9 | 4.7 | 4.7 |
| ZnOct | 0.0 | 1.1 | 2.2 | 3.1 | 4.1 |
| Total Wt. % | 100.0 | 100.0 | 100.0 | 100.0 | 100.0 |
| Cured Appearance | CY | OWF | OWF | OWF | OWF |

TABLE 4B

| Components | Ex. 4-6 | Ex. 4-7 | Ex. 4-8 | Ex. 4-9 | Ex. 4-10 |
|---|---|---|---|---|---|
| BKC | 1.0 | 1.0 | 1.0 | 1.0 | 1.0 |
| DINCH | 46.6 | 46.1 | 45.6 | 45.1 | 44.6 |
| PVC | 47.6 | 47.0 | 46.5 | 46.1 | 45.7 |
| TIDP | 4.8 | 4.9 | 4.8 | 4.7 | 4.7 |
| ZnOct | 0 | 1.0 | 2.1 | 3.1 | 4.0 |
| Total Wt. % | 100.0 | 100.0 | 100.0 | 100.0 | 100.0 |
| Cured Appearance | OB | SCg* | SC to OWg* | C to OWg* | OW | g* = a few small gas bubbles

TABLE 4C

| Components | Ex. 4-11 | Ex. 4-12 | Ex. 4-13 | Ex. 4-14 | Ex. 4-15 |
|---|---|---|---|---|---|
| BKC | 2.0 | 2.0 | 2.0 | 2.0 | 2.0 |
| DINCH | 46.1 | 45.4 | 45.2 | 44.6 | 44.1 |
| PVC | 47.0 | 46.9 | 46.0 | 45.6 | 45.3 |

TABLE 4C-continued

| Components | Ex. 4-11 | Ex. 4-12 | Ex. 4-13 | Ex. 4-14 | Ex. 4-15 |
|---|---|---|---|---|---|
| TIDP | 4.9 | 4.7 | 4.8 | 4.7 | 4.5 |
| ZnOct | 0 | 1.0 | 2.0 | 3.1 | 4.1 |
| Total Wt. % | 100.0 | 100.0 | 100.0 | 100.0 | 100.0 |
| Cured Appearance | OB | CYG** w/black spots | CYG** | C to OWG** | C to OW |

G** = a few large gas bubbles

TABLE 4D

| Components | Ex. 4-16 | Ex. 4-17 | Ex. 4-18 | Ex. 4-19 | Ex. 4-20 |
|---|---|---|---|---|---|
| BKC | 3.0 | 3.0 | 3.0 | 3.0 | 3.0 |
| DINCH | 45.3 | 45.1 | 44.5 | 44.0 | 43.7 |
| PVC | 47.0 | 46.1 | 45.7 | 45.2 | 44.9 |
| TIDP | 4.7 | 4.7 | 4.7 | 4.7 | 4.4 |
| ZnOct | 0 | 1.1 | 2.1 | 3.1 | 4.0 |
| Total Wt. % | 100.0 | 100.0 | 100.0 | 100.0 | 100.0 |
| Cured Appearance | OB | OB | CY shiny | CY to W, shiny | CY to W, shiny |

TABLE 4E

| Components | Ex. 4-21 | Ex. 4-22 | Ex. 4-23 | Ex. 4-24 | Ex. 4-25 |
|---|---|---|---|---|---|
| BKC | 4.0 | 4.0 | 4.0 | 4.0 | 4.0 |
| DINCH | 44.9 | 44.6 | 43.7 | 43.7 | 43.0 |
| PVC | 46.4 | 45.7 | 45.3 | 44.7 | 44.3 |
| TIDP | 4.7 | 4.7 | 5.0 | 4.6 | 4.6 |
| ZnOct | 0 | 1.0 | 2.0 | 3.0 | 4.1 |
| Total Wt. % | 100.0 | 100.0 | 100.0 | 100.0 | 100.0 |
| Cured Appearance | OBSG*** | OB | OB | OB | CYSG*** |

G*** = many large gas bubbles

Example 4 showed that BKC can be incorporated into the flexible PVC plastisol used in a range from 0 to 4 wt %, and more preferably from 0 to 2 wt %. To avoid degradation with flexible PVC formulations containing BKC, similar to those produced in this example, a minimum weight ratio of 1:1 and more preferably 2:1 of ZnOct to BKC should be used.

Example 5

Example 5 varied the concentration of BKC, ZnOct, and octanoic acid at 0, 2, and 4 wt %. Octanoic acid, also known as 2-ethylhexanoic acid is available from Alfa Aesar; Ward Hill, Mass., USA. The sample preparation procedure was the same as that for Example 4. In addition to documenting the appearance of the cured PVC material, as described in Example 4, the appearance of solubility of composition in vehicle (prior to the addition of PVC) was also observed and documented with the following abbreviations: clear=soluble, hazy=partially soluble; insol.=insoluble. Example 5 samples 1-3, 10-12, 19-21 had no BKC and so represented control samples.

TABLE 5A

| Components | Ex. 5-1 | Ex. 5-2 | Ex. 5-3 | Ex. 5-4 | Ex. 5-5 | Ex. 5-6 | Ex. 5-7 | Ex. 5-8 | Ex. 5-9 |
|---|---|---|---|---|---|---|---|---|---|
| BKC | 0 | 0 | 0 | 2.0 | 2.0 | 2.0 | 4.0 | 4.0 | 4.0 |
| DINCH | 47.0 | 45.9 | 44.9 | 46.1 | 45.2 | 44.1 | 44.9 | 43.7 | 43.0 |
| PVC | 48.2 | 47.0 | 46.3 | 47.1 | 46.0 | 45.3 | 46.5 | 45.3 | 44.4 |
| TIDP | 4.8 | 4.9 | 4.7 | 4.9 | 4.8 | 4.5 | 4.7 | 5.0 | 4.6 |
| ZnOct | 0 | 2.2 | 4.1 | 0 | 2.0 | 4.1 | 0 | 2.0 | 4.1 |
| Total Wt. % | 100 | 100 | 100 | 100 | 100 | 100 | 100 | 100 | 100 |
| Solubility in vehicle | clear | clear | clear | insol. | hazy | hazy | insol. | hazy | hazy |
| Cured Appearance | CY | C/OW | OW | OBg | CW/Yg | CWg | OBg | OBG | CYg |

TABLE 5B

| Components | Ex. 5-10 | Ex. 5-11 | Ex. 5-12 | Ex. 5-13 | Ex. 5-14 | Ex. 5-15 | Ex. 5-16 | Ex. 5-17 | Ex. 5-18 |
|---|---|---|---|---|---|---|---|---|---|
| BKC | 0 | 0 | 0 | 2.0 | 2.0 | 2.0 | 4.0 | 4.0 | 4.0 |
| DINCH | 45.9 | 45.2 | 43.8 | 45.0 | 43.9 | 43.1 | 44.2 | 43.0 | 42.0 |
| PVC | 47.2 | 46.0 | 45.5 | 46.2 | 45.5 | 44.3 | 45.1 | 44.5 | 43.7 |
| TIDP | 4.9 | 4.7 | 4.5 | 4.6 | 4.5 | 4.4 | 4.6 | 4.4 | 4.4 |
| ZnOct | 0 | 2.0 | 4.1 | 0 | 2.0 | 4.1 | 0 | 2.0 | 3.9 |
| Octanoic Acid | 2.0 | 2.1 | 2.1 | 2.0 | 2.1 | 2.1 | 2.1 | 2.1 | 2.0 |
| Total Wt. % | 100 | 100 | 100 | 100 | 100 | 100 | 100 | 100 | 100 |
| Solubility in vehicle | clear | clear | clear | hazy | clear | clear | insol. | clear | clear |
| Cured Appearance | CY | OW | OW | OB | CY | CW | OB | OB | CYg |

TABLE 5C

| Components | Ex. 5-19 | Ex. 5-20 | Ex. 5-21 | Ex. 5-22 | Ex. 5-23 | Ex. 5-24 | Ex. 5-25 | Ex. 5-26 | Ex. 5-27 |
|---|---|---|---|---|---|---|---|---|---|
| BKC | 0 | 0 | 0 | 2.0 | 2.0 | 2.0 | 4.0 | 4.0 | 4.0 |
| DINCH | 44.8 | 44.0 | 43.0 | 43.9 | 42.8 | 42.0 | 43.3 | 41.8 | 41.4 |
| PVC | 46.4 | 45.2 | 44.5 | 45.6 | 44.8 | 43.6 | 44.2 | 43.4 | 42.1 |
| TIDP | 4.7 | 4.6 | 4.5 | 4.5 | 4.4 | 4.4 | 4.5 | 4.6 | 4.4 |

TABLE 5C-continued

| Components | Ex. 5-19 | Ex. 5-20 | Ex. 5-21 | Ex. 5-22 | Ex. 5-23 | Ex. 5-24 | Ex. 5-25 | Ex. 5-26 | Ex. 5-27 |
|---|---|---|---|---|---|---|---|---|---|
| ZnOct | 0 | 2.15 | 3.92 | 0 | 2.04 | 4.09 | 0 | 2.18 | 4.06 |
| Octanoic Acid | 4.04 | 4.04 | 4.07 | 4.10 | 3.99 | 3.96 | 4.09 | 4.08 | 4.00 |
| Total Wt. % | 100 | 100 | 100 | 100 | 100 | 100 | 100 | 100 | 100 |
| Solubility in vehicle | clear | clear | clear | clear | clear | clear | insol. | clear | clear |
| Cured Appearance | CY | OW | OW | OBg | CY | CW | OBg | OB | CYg |

It was observed that gas pocket formation associated with increased levels of BKC decreases with increasing amounts of octanoic acid. Gas pockets, while aesthetically undesirable, may also be further evidence of degradation.

Example 6

Example 6 was prepared in the same manner as Examples 4 and 5. Two formulations were evaluated that both contained BKC at 1.5 wt % and ZnOct at 3 wt %. However the octanoic acid content was different in each, at 0 and 1.5 wt %.

TABLE 6

| Components | Ex. 6-1 | Ex. 6-2 |
|---|---|---|
| BKC | 1.5 | 1.5 |
| DINCH | 44.8 | 43.9 |
| PVC | 45.9 | 45.5 |
| TIDP | 4.6 | 4.5 |

TABLE 6-continued

| Components | Ex. 6-1 | Ex. 6-2 |
|---|---|---|
| ZnOct | 3.2 | 3.1 |
| Octanoic Acid | 0 | 1.5 |
| Total Wt. % | 100.0 | 100.0 |
| Cured Appearance | clear/yellow with small gas pockets | clear/almost colorless with little to no gas pockets |

Example 7

Example 7 was conducted to assess the ratios of plasticizer to cationic antimicrobial to primary heat stabilizer of flexible PVC plastisol formulations. The weight percent of components used in the formulations for the flexible PVC plastisol samples of Example 7 are shown in Table 7, below. The order of addition was BKC, DINCH, ESO, TIDP, ZnOct, and then PVC. The BKC, DINCH, ESO, TIDP and ZnOct were added to 25 mL vials. The vials were then mixed well and placed in an oven at 80° C. for ten minutes. After removal from the oven, observations were made of the sample solutions. It was observed that as the amount of plasticizer (DINCH) decreased, the clarity of the sample also decreased. All Example 7 samples appeared to be in solution (no solids were observed), prior to the addition of PVC.

PVC (PVC resin) was added last and then mixed by hand before placing the samples on rollers set at 15 rpm for several hours to thoroughly mix the plastisols. Examples 7-5, 7-6 and 7-7 were noted to be very viscous. The plastisols were then dispensed into aluminum weigh dishes and cured at 177° C. (350° F.) for 10 minutes.

TABLE 7

| Components | Ex. 7-1 | Ex. 7-2 | Ex. 7-3 | Ex. 7-4 | Ex. 7-5 | Ex. 7-6 | Ex. 7-7 |
|---|---|---|---|---|---|---|---|
| BKC | 1.2 | 1.5 | 1.5 | 1.5 | 2.0 | 1.55 | 1.6 |
| DINCH | 50.5 | 50.1 | 49.8 | 36.6 | 12.8 | 12.8 | 13.0 |
| PVC | 36.0 | 35.7 | 35.6 | 45.8 | 63.1 | 63.3 | 64.2 |
| ESO | 6.3 | 6.4 | 6.2 | 8.0 | 11.3 | 11.3 | 11.4 |
| TIDP | 3.6 | 3.7 | 3.7 | 4.7 | 6.3 | 6.5 | 6.4 |
| ZnOct | 2.5 | 2.6 | 3.3 | 3.3 | 4.5 | 4.6 | 3.4 |
| Total Wt. % | 100.0 | 100.0 | 100.0 | 100.0 | 100.0 | 100.0 | 100.0 |
| Solution appearance | semi-clear | semi-clear | semi-clear | hazy | opaque/white/viscous | opaque/white/viscous | opaque/white/viscous |
| DINCH:BKC | 44:1 | 33:1 | 33:1 | 25:1 | 6:1 | 8:1 | 8:1 |
| DINCH:Zn Oct | 20:1 | 19:1 | 15:1 | 11:1 | 3:1 | 3:1 | 4:1 |
| ZnOct:BKC | 2:1 | 1.7:1 | 2:1 | 2:1 | 2:1 | 3:1 | 2:1 |
| Cured appearance | S, Y, g | S, Y, g | S, Y, g | F, Y, G | H, Y, O, S | H, Y, O, S | H, Y, O, S |

Texture: S = very soft; F = flexible; H = Hard
Color: Y = light yellow; O = opaque; S = oily surface
Air/gas bubble entrapment: g = only a few gas bubbles; G = gas bubbles Example 8

Example 8 was conducted to assess if additional heat stabilizer is needed to reduce the degradation of the flexible PVC brought about by the presence of various antimicrobial agents. The antimicrobials evaluated were benzethonium chloride (BZT), octenidine dihydrochloride (OCT), PCMX, 2-phenoxyethanol (POEtOH), and polyhexamethylene biguanide (PHMB). The antimicrobial agent was dispensed into a 20 mL vial. To this vial were added MESAMOLL, TIDP, and ZnOct, in that order. The vial was then capped and vortexed for several seconds, and then placed on rollers set at 65 rpm for several hours to promote the dissolution of the antimicrobial. Next, 5 grams of PVC was added and the samples were mixed well by hand and then rolled to ensure uniformity at 40 rpm for 1 hour. The samples were then poured into aluminum weigh dishes and cured at 177° C. (350° F.) for 10 minutes. For Example 8, the amount of each antimicrobial agent added was calculated to be equal to the same number of moles of BKC at 1.5 wt % in a plastisol formulation.

Abbreviations for the results of Example 8, appearance of composition in vehicle before and after curing: C=clear; O=opaque; Y=yellow; DY=dark yellow/orange; W=white; B-black; s=suspension; ppt=precipitate/insoluble

TABLE 8A

| Components | Ex. 8-1 | Ex. 8-2 | Ex. 8-3 | Ex. 8-4 | Ex. 8-5 | Ex. 8-6 |
|---|---|---|---|---|---|---|
| BZT | 1.8 | 1.8 | 1.7 | 0 | 0 | 0 |
| OCT | 0 | 0 | 0 | 2.5 | 2.5 | 2.4 |
| MESAMOLL | 45.6 | 44.7 | 43.5 | 45.1 | 44.1 | 43.3 |
| PVC | 46.7 | 45.6 | 45.1 | 46.4 | 45.5 | 43.9 |
| TIDP | 4.7 | 4.6 | 4.5 | 4.8 | 4.6 | 5.2 |
| ZnOct | 1.2 | 3.3 | 5.2 | 1.2 | 3.3 | 5.2 |
| Total Wt. % | 100.0 | 100.0 | 100.0 | 100.0 | 100.0 | 100.0 |
| Solution appearance | OY | C | C | OWs | OWs | OWs |
| Cured appearance | B dots | C | C | DY | Y/DY | Y |

TABLE 8B

| Components | Ex. 8-7 | Ex. 8-8 | Ex. 8-9 | Ex. 8-10 | Ex. 8-11 | Ex. 8-12 |
|---|---|---|---|---|---|---|
| PCMX | 0.6 | 0.6 | 0.6 | 0 | 0 | 0 |
| POEtOH | 0 | 0 | 0 | 0.6 | 0.6 | 0.5 |
| MESAMOLL | 46.0 | 44.7 | 43.9 | 45.7 | 44.8 | 44.0 |
| PVC | 47.4 | 46.8 | 45.7 | 47.7 | 46.5 | 45.6 |
| TIDP | 4.7 | 4.6 | 4.5 | 4.8 | 4.7 | 4.6 |
| ZnOct | 1.3 | 3.3 | 5.3 | 1.2 | 3.4 | 5.3 |
| Total Wt. % | 100.0 | 100.0 | 100.0 | 100.0 | 100.0 | 100.0 |
| Solution appearance | C | C | C | C | C | C |
| Cured appearance | OW | OW | OW | OW | OW | OW |

TABLE 8C

| Components | Ex. 8-13 | Ex. 8-13 | Ex. 8-15 |
|---|---|---|---|
| PHMB | 5.6 | 5.5 | 5.4 |
| MESAMOLL | 44.0 | 42.5 | 41.7 |
| PVC | 44.5 | 44.2 | 43.6 |
| TIDP | 4.7 | 4.5 | 4.3 |
| ZnOct | 1.2 | 3.3 | 5.0 |
| Total Wt. % | 100.0 | 100.0 | 100.0 |
| Solution appearance | OWppt | OWppt | OWppt |
| Cured appearance | Ow | Ow | Ow |

It was observed that BZT was not soluble in MESAMOLL at low concentrations of ZnOCT. However, with increasing amounts of ZnOct, solubility was improved and decreased heat degradation was observed. OCT was not soluble in MESAMOLL, even with increasing amounts of ZnOct. There did appear to be less degradation of the OCT in the cured PVC with increasing amounts of ZnOct. For some antimicrobial agents such as PCMX or POEtOH, this effect was not observed, probably because these antimicrobials appeared to have been well below their solubility limits in MESAMOLL.

Antimicrobial Efficacy Test

The following procedures were used for the microbiological assessment of subsequent examples of antimicrobial PVC compositions. The following materials were used in the microbiological test procedure: Tryptic Soy Broth (TSB), available from Becton, Dickinson and Company (BD) of Franklin Lakes, N.J. (USA), under the tradename BACTO; D/E Neutralizing Broth, available from BD under the tradename DIFCO; BD Falcon 50 mL Polypropylene Conical Test Tubes, available from BD; Mini Flip-Top Vial with Butterfields Buffer, available from 3M Company of St. Paul, Minn. (USA); and PETRIFILM Aerobic Count Plate (AC) 6406, available from 3M Company of St. Paul, Minn. (USA);

A culture of *S. aureus* ATCC 25923 (or other specified bacteria) in 20 mL of TSB was obtained fresh, overnight (18-24 hours). The working bacterial stock solution was prepared: transferred 1 mL of the prepared culture to 9 mL of Butterfields Buffer (1:10 dilution). The samples were arranged in triplicate into empty, sterile Petri dishes to support the samples and decrease unwanted contamination from the environment. Each sample was inoculated with 100 µL of the working stock by pipetting 12 dots on the surface. The closed Petri dishes were placed with inoculated samples into a plastic container with a wet paper towel placed in the bottom of the container, to create a high humidity environment during incubation. The container, with samples inside, was sealed with the lid and placed into an incubator at 28° C. for the designated contact time, typically 1 or 2 hours, etc., (+/−0.1 hours). The "0 minute controls" were kept out. Tweezers that were pre-cleaned with alcohol before and between samples were used to carefully lift the samples out of the Petri dishes and put them into the 50 mL conical tubes that were previously filled with 20 mL of D/E neutralizing broth. Samples were sonicated in the conical tubes for 2 minutes in a water bath sonicator. The samples were further vortexed in the tubes for 1 minute at a high speed setting of "9" on the vortexer. The samples were diluted with a 1:10 serial dilution using the Butterfields Buffer test tubes. The dilutions were completed by adding 1 mL of the sample fluid into 9 mL of Butterfields Buffer for the 1:10 dilution.

Next, 1 mL from the 1:10 dilution tube was pipetted into 9 mL of Butterfields Buffer to make the 1:100 dilution. Then, pipetted 1 mL from the 1:100 dilution tube into 9 mL of Butterfields Buffer for a 1:1000 dilution. Finally, pipetted 1 mL from the 1:1000 dilution tube into 9 mL of Butterfields Buffer for a 1:10000 dilution. The samples were plated by vortexing the sample and dilution tubes between transfers and pipetting 1 mL aliquots from these tubes onto the PETRIFILM Aerobic Count Plate. The plating process was completed for the Neat (no dilution, 1 mL taken directly from the sample) to negative four (−4) dilutions, which are also notated as 1:1, 1:10 1:100 1:1000, 1:10000. The samples were neutralized after the designated time point in 10 mL DE broth and used the same plating technique to plate them onto PETRIFILM. The samples were placed in a 37° incubator for 24 hours, then, read with a PETRIFILM PLATE READER (available from 3M Company of St. Paul, Minn.) and the number of colonies recorded and reported as Log(10) Recovery. In some instances Log(10) Reduction was also calculated and reported. Log Reduction is calculated by subtracting the log recovered from the input control.

Example 9

Example 9 was conducted to evaluate the antimicrobial efficacy of various flexible PVC formulations with different antimicrobial agents. The antimicrobial agents assessed were BKC, BZT, OCT, PCMX, POEtOH, and PHMB. The amount of each antimicrobial agent added was calculated to be equal to the same number of moles of BKC at 1.5 wt % in the plastisol formulation. The antimicrobial agent was added into a 120 mL (4 fluid ounces) glass container. To this container were added DINCH, TIDP, ZnOct, and octanoic acid in that order. The container was capped and vortexed for several seconds, and then placed on rollers set at 65 rpm for approximately 2 hours to promote the dissolution of the antimicrobial agent. To all of the samples 15 grams of PVC was added and the samples were mixed well by hand and then were rolled to ensure uniformity at 40 rpm overnight.

The Example 9 formulations showed a range of solubilities of the antimicrobial agent in the vehicle before the addition of PVC resin. Example 9-3 was not completely dissolved, the solution was white, but with no visible precipitation. Example 9-4, BZT appeared to be slightly less soluble than Example 9-3 with BKC. For Example 9-5, OCT was much less soluble than BKC. In Example 9-6 the PCMX appeared to be completely dissolved. In Examples 9-7 the phenoxyethanol appeared to be completely dissolved. In Example 9-8 the PHMB was much less soluble than the BKC of Example 9-3. In Example 9-8, the BKC appeared to be completely dissolved in the presence of octanoic acid.

After the overnight mixing, the samples were then poured into 7 cm diameter aluminum weigh dishes and cured at 177° C. (350° F.) for 10 minutes. Each container of sample made two 14 gram flexible PVC samples ("pucks") of about 7 cm in diameter and about 3.4 mm thick. After curing the samples were subjected to running water for 10 minutes, five minutes on each side of the flexible PVC puck. The flexible PVC samples were blotted dry with a paper towel and three circular punches were cut from each sample for triplicate testing in the microbiological test procedure described above. The circular punches were 2.5 cm (1 inch) in diameter.

The Antimicrobial Efficacy Test procedure was performed on the side of the sample that was exposed to air during curing, except for the samples containing OCT, which appeared to have some degree of degradation on that surface. In those cases, (OCT) the microbiological testing was performed on the side that was the interface between the plastisol and the aluminum dish during curing. During the inoculation of the cured PVC with the bacteria working solution, the apparent hydrophobicity of the PVC surface was observed. Some samples appeared to have a hydrophobic surface because the solution beaded or did not "wet" the surface. Other sample surfaces appeared hydrophilic because the solution easily spread or "wet" the PVC sample surface. The Working Stock Solution of S. aureus for Example 9 had an Average Log(10) Recovery of 7.99 with a Std Dev of 0.04.

TABLE 9A

| Components | Ex. 9-1 Control | Ex. 9-2 Control | Ex. 9-3 | Ex. 9-4 | Ex. 9-5 |
|---|---|---|---|---|---|
| BKC | 0 | 0 | 1.5 | 0 | 0 |
| BZT | 0 | 0 | 0 | 1.8 | 0 |
| OCT | 0 | 0 | 0 | 0 | 2.4 |
| DINCH | 47.9 | 44.5 | 44.8 | 43.6 | 43.3 |
| PVC | 49.2 | 45.6 | 45.9 | 44.9 | 44.5 |
| TIDP | 1.6 | 4.6 | 4.6 | 4.5 | 4.5 |
| ZnOct | 1.2 | 5.3 | 3.2 | 5.2 | 5.3 |
| Total Wt. % | 100.0 | 100.0 | 100.0 | 100.0 | 100.0 |
| Solution wets surface | no | no | yes | yes | yes |
| Ave. Log Recovery. at 0 minutes | 5.5 | 5.6 | 5.5 | 5.6 | 5.3 |
| Std Dev (at 0 min) | 0.05 | 0.09 | 0.05 | 0.06 | 0.05 |
| Ave. Log Recovery at 60 minutes | 5.6 | 5.5 | 0.1 | 0.1 | 0.1 |
| Std Dev (at 60 min) | 0.07 | 0.06 | 0.19 | 0.12 | 0.21 |
| Ave. Log Reduction at 60 minutes | N/A | N/A | 5.4 | 5.5 | 5.4 |

TABLE 9B

| Components | Ex. 9-6 | Ex. 9-7 | Ex. 9-8 |
|---|---|---|---|
| BKC | 0 | 0 | 1.47 |
| PCMX | 0.7 | 0 | 0 |
| POEtOH | 0 | 0.6 | 0 |
| PHMB | 0 | 0 | 0 |
| DINCH | 47.6 | 47.5 | 43.9 |
| PVC | 48.8 | 49.1 | 45.4 |
| TIDP | 1.7 | 1.6 | 4.5 |
| ZnOct | 1.2 | 1.2 | 3.1 |
| Octanoic Acid | 0 | 0 | 1.5 |
| Total Wt. % | 100.0 | 100.0 | 100.0 |
| Solution wets surface? | NO | NO | yes |
| Ave. Log Recovery. at 0 minutes | 5.7 | 5.7 | 5.5 |
| Std Dev (at 0 min) | 0.06 | 0.05 | 0.11 |
| Ave. Log Recovery at 60 minutes | 5.7 | 5.6 | 0.1 |
| Std Dev (at 60 min) | 0.07 | 0.03 | 0.12 |
| Ave. Log Reduction at 60 minutes | −0.2 | −0.1 | 5.47 |

Example 10

Example 10 samples were prepared and evaluated in the same fashion as Examples 9. The Working Stock Solution for Example 10 had an Average Log(10) Recovery of 7.8 with a Std Dev of 0.03. The Input Control had an Ave. Log(10) Recovery of 5.4 with a Std Dev of 0.03. All of the Example 10 samples containing 1.5 wt % BKC showed complete kill in 60 minutes

TABLE 10A

| Components | Ex. 10-1 | Ex. 10-2 | Ex. 10-3 | Ex. 10-4 | Ex. 10-5 | Ex. 10-6 |
|---|---|---|---|---|---|---|
| BKC | 0 | 1.5 | 0 | 1.5 | 0 | 1.5 |
| DEHP | 38.0 | 36.5 | 0 | 0 | 19.0 | 18.4 |
| BBP | 0.0 | 0.0 | 38.1 | 36.6 | 19.0 | 18.4 |
| PVC | 47.8 | 46.0 | 47.8 | 45.9 | 47.9 | 45.9 |
| ESO | 8.4 | 8.1 | 8.3 | 8.0 | 8.3 | 8.0 |
| di-IDPP | 4.8 | 4.6 | 4.8 | 4.7 | 4.8 | 4.6 |
| ZnOct | 1.0 | 3.3 | 1.0 | 3.3 | 1.0 | 3.2 |
| Total Wt % | 100.0 | 100.0 | 100.0 | 100.0 | 100.0 | 100.0 |
| Solution Appearance | Clear/colorless | Clear/white | Clear/colorless | Clear/colorless | Clear/colorless | Clear/light white |
| Cured Appearance | Clear | Clear/light yellow* | Clear | Clear/light yellow* | Clear | Clear/light yellow* |
| Ave. Log Recovery. at 0 min | 5.4 | NT | 5.4 | NT | 5.4 | NT |

TABLE 10A-continued

| Components | Ex. 10-1 | Ex. 10-2 | Ex. 10-3 | Ex. 10-4 | Ex. 10-5 | Ex. 10-6 |
|---|---|---|---|---|---|---|
| Std Dev (at 0 min) | 0.05 | NT | 0.04 | NT | 0.04 | NT |
| Ave. Log Recovery at 60 minutes | 5.4 | 0.00 | 5.4 | 0.00 | 5.4 | 0.00 |
| Std Dev (at 60 min) | 0.02 | 0.00 | 0.06 | 0.00 | 0.02 | 0.00 |

*small gas bubbles
NT = not tested

TABLE 10B

| Components | Ex. 10-7 | Ex. 10-8 | Ex. 10-9 | Ex. 10-10 |
|---|---|---|---|---|
| BKC | 0 | 1.5 | 0 | 1.5 |
| Mesomall II | 0 | 0 | 19.1 | 18.5 |
| DPGDB | 38.3 | 36.5 | 18.8 | 18.2 |
| PVC | 47.5 | 45.8 | 47.4 | 45.8 |
| ESO | 8.3 | 8.0 | 8.9 | 8.2 |
| di-IDPP | 4.9 | 4.6 | 4.9 | 4.6 |
| ZnOct | 1.0 | 3.6 | 0.9 | 3.2 |
| Total Wt % | 100.0 | 100.0 | 100.0 | 100.0 |
| Solution Appearance | Clear/colorless | Clear/very light yellow | Clear/light yellow | Clear/slight haze/light yellow |
| Cured Appearance | Clear | Clear/light yellow* | Clear | Clear/light yellow* |
| Ave. Log Recovery. at 0 minutes | 5.3 | NT | 5.4 | NT |
| Std Dev (at 0 min) | 0.03 | NT | 0.06 | NT |
| Ave. Log Recovery at 60 minutes | 5.4 | 0.0 | 5.5 | 0.0 |
| Std Dev (at 60 min) | 0.03 | 0.0 | 0.05 | 0.0 |

*small gas bubbles

Example 11

Example 11 was prepared and evaluated in the same fashion as Example 9 except that gram negative *E. coli* ATCC 25922 was used to assess the antimicrobial efficacy of the flexible PVC formulations. The Input Control for Example 11 had an Average Log(10) Recovery of 5.4 with a Std Dev of 0.03.

TABLE 11

| Components | Ex. 11-1 (Control) | Ex. 11-2 |
|---|---|---|
| BKC | 0 | 1.5 |
| DINCH | 37.3 | 36.7 |
| PVC | 46.7 | 46.0 |
| ESO | 8.1 | 8.0 |
| TIDP | 4.6 | 4.6 |
| ZnOct | 3.3 | 3.2 |
| Total Wt. % | 100.0 | 100.0 |
| Ave. Log Recovery. at 0 hrs | 5.7 | 5.7 |
| Std Dev (at 0 hrs) | 0.07 | 0.09 |
| Ave Log REDUCTION at 2 hrs | 0.6 | 5.9 |
| Std Dev (at 2 hrs) | 0.04 | 0.0 |
| Ave Log REDUCTION at 4 hrs | 0.8 | 5.9 |
| Std Dev (at 4 hrs) | 0.03 | 0.0 |

Example 12

Example 12 was also prepared and evaluated in the same fashion as Example 9. The antimicrobial efficacies of the flexible PVC formulations were evaluated against *S. aureus* (ATCC25923) after 2 hours of contact. The Working Stock Solution for Example 12 had an Average Log(10) Recovery of 7.99 with a Std Dev of 0.07. The Input Control had an Average Log(10) Recovery of 6.0 with a Std Dev of 0.03.

TABLE 12A

| Components | Ex. 12-1* | Ex. 12-2 | Ex. 12-3 | Ex. 12-4 | Ex. 12-5 | Ex. 12-6 | Ex. 12-7 |
|---|---|---|---|---|---|---|---|
| BKC | 0 | 0.2 | 0.5 | 0.7 | 1.0 | 1.3 | 1.5 |
| DINCH | 40.0 | 39.9 | 39.7 | 39.6 | 40.8 | 39.5 | 39.4 |
| PVC | 50.0 | 49.9 | 49.8 | 49.7 | 48.0 | 49.3 | 49.2 |
| TIDP | 5.0 | 5.0 | 5.0 | 5.0 | 5.1 | 4.9 | 4.9 |
| ZnOct | 3.5 | 3.5 | 3.5 | 3.5 | 3.6 | 3.5 | 3.5 |
| Octanoic acid | 1.5 | 1.5 | 1.5 | 1.5 | 1.5 | 1.5 | 1.5 |
| Total Wt % | 100.0 | 100.0 | 100.0 | 100.0 | 100.0 | 100.0 | 100.0 |
| Average Log Reduction at 2 hours | 0.2 | 0.6 | 0.9 | 2.2 | 2.9 | 6.0 | 6.0 |
| Std Dev (at 2 hrs) | 0.05 | 0.34 | 0.07 | 0.11 | 0.09 | 0.00 | 0.00 |

*Control - no antimicrobial agent.

TABLE 12B

| Components | Ex. 12-8A* | Ex. 12-8B | Ex. 12-9 | Ex. 12-10 | Ex. 12-11 | Ex. 12-12 |
|---|---|---|---|---|---|---|
| OCT | 0.5 | 0.5 | 0.5 | 0.5 | 0.5 | 0.5 |
| ESO | 0 | 0 | 1.5 | 1.5 | 0 | 0 |
| Octanoic acid | 0 | 0 | 0 | 0 | 1.5 | 1.5 |
| DINCH | 40.5 | 40.5 | 39.8 | 39.8 | 39.8 | 39.8 |
| PVC | 50.5 | 50.5 | 49.7 | 49.7 | 49.7 | 49.7 |
| TIDP | 5.0 | 5.0 | 5.0 | 5.0 | 5.0 | 5.0 |
| ZnOct | 3.5 | 3.5 | 3.5 | 3.5 | 3.5 | 3.5 |
| Total Wt. % | 100.0 | 100.0 | 100.0 | 100.0 | 100.0 | 100.0 |

TABLE 12B-continued

| Components | Ex. 12-8A* | Ex. 12-8B | Ex. 12-9 | Ex. 12-10 | Ex. 12-11 | Ex. 12-12 |
|---|---|---|---|---|---|---|
| Ave Log Reduction at 2 hrs | −0.02* | 5.1 | 4.1 | 3.5 | 6.0 | 6.0 |
| Std Dev (at 2 hrs) | 0.10* | 0.85 | 0.10 | 2.04 | 0.00 | 0.00 |

*Example 12-8A was equivalent to Ex. 12-8B except that 12-8A was evaluated at time 0. All other samples were evaluated after 2 hours of contact time.

Example 13

Example 13 was also prepared and evaluated in the same fashion as Example 9. The antimicrobial efficacies of the flexible PVC formulations were evaluated against *S. aureus* (ATCC25923) after 2 hours of contact. The Working Stock Solution for Example 13 had an Average Log(10) Recovery of 7.69 with a Std Dev of 0.08. The Input Control had an Ave Log(10) Recovery of 5.66 with a Std Dev of 0.05.

TABLE 13A

| Components | Ex. 13-1A* | Ex. 13-1B | Ex. 13-2 | Ex. 13-3 | Ex. 13-4 | Ex. 13-5 |
|---|---|---|---|---|---|---|
| OCT | 0 | 0 | 0.2 | 0.5 | 1.0 | 1.5 |
| DINCH | 40.6 | 40.6 | 40.5 | 40.4 | 40.2 | 40.0 |
| PVC | 50.7 | 50.8 | 50.7 | 50.5 | 50.3 | 50.0 |
| TIDP | 5.1 | 5.1 | 5.1 | 5.1 | 5.0 | 5.0 |
| ZnOct | 3.6 | 3.5 | 3.5 | 3.5 | 3.5 | 3.5 |
| Total Wt % | 100.0 | 100.0 | 100.0 | 100.0 | 100.0 | 100.0 |
| Ave Log Reduction at 2 hrs | 0.1* | 0.3 | 3.3 | 4.6 | 5.7 | 5.7 |
| Std Dev (at 2 0 hrs) | 0.04* | 0.04 | 0.91 | 1.71 | 0.00 | 0.00 |

*Example 13-1A was equivalent to Ex. 13-1B except that 13-1A was evaluated at time 0. All other samples were evaluated after 2 hours of contact time.

TABLE 13B

| Components | Ex. 13-6 | Ex. 13-7 | Ex. 13-8 | Ex. 13-9 |
|---|---|---|---|---|
| BKC | 0.2 | 0.5 | 1.0 | 1.5 |
| DINCH | 40.5 | 40.4 | 40.2 | 40.0 |
| PVC | 50.7 | 50.5 | 50.3 | 50.0 |
| TIDP | 5.1 | 5.1 | 5.0 | 5.0 |
| ZnOct | 3.5 | 3.5 | 3.5 | 3.5 |
| Total Wt % | 100.0 | 100.0 | 100.0 | 100.0 |
| Ave Log Reduction at 2 hrs | 0.5 | 2.6 | 3.9 | 5.7 |
| Std Dev (at 2 hrs) | 0.05 | 0.11 | 0.03 | 0.00 |
| Sample ID | 6 2 hr | 7* 2 hr | 8 2 hr | 9* 2 hr |

Example 14

Example 14 was also prepared and evaluated in the same fashion as Example 9. The antimicrobial efficacies of the flexible PVC formulations were evaluated against *S. aureus* (ATCC25923) after 2 hours of contact. The Working Stock Solution for Example 14 had an Average Log(10) Recovery of 7.89 with a Std Dev of 0.05. The Input Control had an Ave Log(10) Recovery of 5.46 with a Std Dev of 0.02.

TABLE 14

| Components | Ex. 14-1A* | Ex. 14-1B | Ex. 14-2 | Ex. 14-3 | Ex. 14-4 | Ex. 14-5 |
|---|---|---|---|---|---|---|
| BKC | 0 | 0 | 0.2 | 0.5 | 1.0 | 1.5 |
| MESAMOLL | 40.6 | 40.6 | 40.5 | 40.4 | 40.2 | 40.0 |
| PVC | 50.8 | 50.8 | 50.7 | 50.5 | 50.3 | 50.0 |
| TIDP | 5.1 | 5.1 | 5.1 | 5.1 | 5.0 | 5.0 |
| ZnOct | 3.5 | 3.5 | 3.5 | 3.5 | 3.5 | 3.5 |
| Total Wt. % | 100.0 | 100.0 | 100.0 | 100.0 | 100.0 | 100.0 |
| Inoculum wets surface? | no | no | yes | yes | YES | YES |
| Ave Log Reduction at 2 hrs | 0.0* | 0.24 | 1.6 | 5.0 | 5.3 | 5.2 |
| Std Dev (at 2 hrs) | 0.06* | 0.12 | 0.12 | 0.42 | 0.28 | 0.34 |

*Example 14-1A was equivalent to Ex. 14-1B except that 14-1A was evaluated at time 0. All other samples were evaluated after 2 hours of contact time.

Example 15

Example 15 was conducted to assess antimicrobial activity in samples of flexible PVC with BKC after being wiped with an alcohol wipe. Example 15 was prepared in a manner similar to Example 9. BKC was added into a 120 mL glass container. To this container were added ZnOct, TIDP, and MESAMOLL in that order. The container was capped and vortexed for several seconds before being uncapped and placed into an oven at 60° C. for five minutes to aid in the dissolution of the BKC particles. After the containers were taken out of the oven, they were recapped and vortexed again for several seconds. For each sample, 50 grams of PVC (same source as Example 3) was added and mixed well by hand and then rolled overnight at 60 rpm at room temperature to ensure swelling of the PVC.

After overnight mixing, 10 grams of sample were poured into each of two 5.7 cm diameter aluminum weigh dishes, and cured for ten minutes at 177° C. (350° F.) to form cured PVC "pucks" with an approximate diameter of 5.7 cm and a thickness of about 3.7 mm. For each weight percent of BKC added (0.5%, 1.0% and 1.5%) one of the pucks was taken and wiped with an alcohol wipe (SANI-HANDS ALC wipe, available from PDI, Inc. of Orangeburg, N.Y. (USA)). It was then let dry for two minutes before being wiped again, this procedure was repeated for a total of 15 times with 15 new wipes.

It was assumed that immediately after cleaning the pucks the BKC on the surface would be wiped away, temporarily reducing the antimicrobial activity of the PVC at the surface. It was also expected that over time more BKC would migrate or "bloom" from the interior of the PVC material to the exterior surface of the puck, thus replenishing the antimicrobial activity of the PVC. Therefore, the pucks were left out overnight to reestablish the antimicrobial activity at the surface of the PVC puck. The next morning three circular punches were cut from each sample for triplicate microbiology testing, according to the Antimicrobial Efficacy Test, described above. The circular punches were 1.6 cm (⅝ inch) in diameter. The antimicrobial efficacies of the flexible PVC formulations of Example 15 were evaluated against *S. aureus* (ATCC25923) after 2 hours of contact, in the same fashion as described above in Example 9. The Working Stock Solution of *S. aureus* for Example 15 had an Average Log(10) Recovery of 7.79 with a Std Dev of 0.06.

TABLE 15

| Components | Ex. 15-1A* | Ex. 15-1B | Ex. 15-2 | Ex. 15-3 | Ex. 15-4 | Ex. 15-5 | Ex. 15-6 | Ex. 15-7 |
|---|---|---|---|---|---|---|---|---|
| BKC | 0.0 | 0.0 | 0.5 | 0.5 | 1.0 | 1.0 | 1.5 | 1.5 |
| Mesamoll | 40.6 | 40.6 | 40.5 | 40.5 | 40.2 | 40.2 | 40.0 | 40.0 |
| PVC | 50.7 | 50.7 | 50.5 | 50.5 | 50.3 | 50.3 | 50.0 | 50.0 |
| TIDP | 5.0 | 5.0 | 5.0 | 5.0 | 5.0 | 5.0 | 5.0 | 5.0 |
| ZnOct | 3.7 | 3.7 | 3.5 | 3.5 | 3.5 | 3.5 | 3.5 | 3.5 |
| Total Wt % | 100.0 | 100.0 | 100.0 | 100.0 | 100.0 | 100.0 | 100.0 | 100.0 |
| Alcohol Wiped? | NO | NO | NO | YES | NO | YES | NO | YES |
| Ave Log Red. at 2 hrs | 0.0 | 0.3 | 4.7 | 2.7 | 5.6 | 5.4 | 5.6 | 5.6 |
| Std Dev (at 2 hrs) | 0.15 | 0.04 | 1.38 | 0.35 | 0.00 | 0.21 | 0.00 | 0.00 |

*Example 15-1A was equivalent to Ex. 15-1B except that 15-1A was evaluated at time 0.
All other samples were evaluated after 2 hours of contact time.

Example 16

Example 16, was prepared and cured in the same way as Example 15. However, the regenerative antimicrobial activity of Example 16 was assessed in a different way. Instead of being wiped with an alcohol wipe, some of the samples of Example 16 were soaked overnight in 70% w/w solution of isopropyl alcohol (IPA). Since most cleaning wipes use 70% IPA and 30% water, a solution of 29.7 grams of deionized water was mixed with 69.3 grams of IPA (isopropyl alcohol, minimum 99.9% purity, available from EMD Millipore Corporation of Billerica, Mass. (USA)). The solution was split and poured into two 240 mL containers. The containers were capped and vortexed briefly to ensure mixing before one puck with 1% BKC was placed into one of the containers and one puck with 1.5% BKC was placed into the other container. The pucks were left overnight to soak in the 70% w/w IPA solution. The next day the pucks were removed from the 70% IPA solution and allowed to air dry for approximately 24 hours at room temperature conditions. Then, three circular punches were cut from each sample for triplicate microbiology testing. The circular punches were 1.6 cm (⅝ inch) in diameter. The antimicrobial efficacies of the flexible PVC formulations of Example 16 were evaluated against *S. aureus* (ATCC25923) after 2 hours of contact, in the same fashion as described above in Example 9. The Working Stock Solution of *S. aureus* for Example 16 had an Average Log(10) Recovery of 8.69 with a Std Dev of 0.01.

TABLE 16

| Components | Ex. 16-1A* | Ex. 16-1B | Ex. 16-2 | Ex. 16-3 | Ex. 16-4 | Ex. 16-5 |
|---|---|---|---|---|---|---|
| BKC | 0.0 | 0.0 | 1.0 | 1.0 | 1.5 | 1.5 |
| Mesamoll | 40.7 | 40.7 | 40.3 | 40.3 | 40.0 | 40.0 |
| PVC | 50.8 | 50.8 | 50.3 | 50.3 | 50.1 | 50.1 |
| TIDP | 5.0 | 5.0 | 5.0 | 5.0 | 5.0 | 5.0 |
| ZnOct | 3.5 | 3.5 | 3.5 | 3.5 | 3.5 | 3.5 |
| Soaked in 70% IPA? | NO | NO | NO | YES | NO | YES |
| Total Wt % | 100.0 | 100.0 | 100.0 | 100.0 | 100.0 | 100.0 |
| Ave Log Red. at 2 hrs | 0.0 | 0.0 | 5.6 | 2.5 | 5.6 | 3.2 |
| Std Dev (at 2 hrs) | 0.06 | 0.07 | 0.00 | 0.19 | 0.00 | 1.21 |

*Example 16-1A was equivalent to Ex. 16-1B except that Ex. 16-1A was evaluated at time 0.
All other samples were evaluated after 2 hours of contact time.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

We claim:

1. A hardenable polyhaloolefin composition, the composition comprising:
    a polyvinyl chloride polymer;
    a cationic antimicrobial agent; and
    a vehicle comprising a plasticizer and a heat stabilizer package, wherein the cationic antimicrobial is dissolved or dispersed in the vehicle to a concentration of at least 0.5 wt. % based on the total weight of the vehicle.

2. The composition of claim 1, wherein the cationic antimicrobial agent comprises at least one of a quaternary ammonium, a polymeric cationic amine, and a biguanide, wherein the cationic antimicrobial agent is present at a concentration of at least about 0.1 wt. % and no greater than about 10 wt. %, based on the total weight of the composition.

3. The composition of claim 1, wherein the heat stabilizer package comprises a primary heat stabilizer, wherein the primary heat stabilizer comprises an alkyl carboxylate salt of zinc, calcium, barium, strontium, magnesium, tin, quaternary amine, or combinations thereof.

4. The composition of claim 3, wherein the primary heat stabilizer comprises zinc dioctoate, wherein the zinc dioctoate is present at a concentration of no greater than about 5 wt. % and at least about 0.5 wt. %, based on the total weight of the composition and wherein the primary heat stabilizer is present at a concentration at least equal to the concentration of the cationic antimicrobial agent.

5. An article comprising:
    an exposed surface at least partially formed from a hardened antimicrobial composition, the composition comprising:
        a polyhaloolefin polymer;
        a heat stabilizer package;
        a plasticizer; and
        a cationic antimicrobial agent incorporated throughout the polyhaloolefin polymer, wherein the cationic antimicrobial is dissolved or dispersed in the vehicle to a concentration of at least 0.5 wt. % based on the total weight of the heat stabilizer package and the plasticizer.

6. The article of claim 5, wherein the article is a medical article.

7. The article of claim 5, wherein the cationic antimicrobial agent comprises at least one of a small molecule quaternary ammonium, a polymeric cationic amine, and a biguanide, and wherein the cationic antimicrobial agent is present at a concentration of at least about 0.1 wt. % and no greater than about 10 wt %, based on the total weight of the composition.

8. The article of claim 5 wherein the heat stabilizer package comprises a primary heat stabilizer, and wherein the primary heat stabilizer comprises a salt of zinc, tin, calcium, barium, strontium, magnesium, quaternary amine, or combinations thereof, and wherein the primary heat stabilizer is present in the composition at a concentration at least equal to the concentration of the cationic antimicrobial agent.

9. The article of claim 5, wherein the cationic antimicrobial agent regenerates at the surface of the article after customary use.

10. The composition of claim 3, wherein the heat stabilizer package further comprises a secondary heat stabilizer comprising, an aryl or alkyl phosphite.

\* \* \* \* \*